(12) United States Patent  
Murthy

(10) Patent No.: US 12,331,279 B2
(45) Date of Patent: *Jun. 17, 2025

(54) SYSTEMS FOR PRODUCING CELLULAR IMMUNOTHERAPEUTICS AND METHODS OF USE THEREOF

(71) Applicant: Northeastern University, Boston, MA (US)

(72) Inventor: Shashi K. Murthy, Newton, MA (US)

(73) Assignee: Northeastern University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/448,031

(22) Filed: Aug. 10, 2023

(65) Prior Publication Data

US 2023/0392106 A1 Dec. 7, 2023

Related U.S. Application Data

(63) Continuation of application No. 17/664,532, filed on May 23, 2022, now Pat. No. 11,767,500, which is a (Continued)

(51) Int. Cl.
*C12M 1/36* (2006.01)
*A61K 39/00* (2006.01)
(Continued)

(52) U.S. Cl.
CPC ......... *C12M 41/48* (2013.01); *A61K 39/0008* (2013.01); *A61K 40/19* (2025.01); (Continued)

(58) Field of Classification Search
None
See application file for complete search history.

(56) References Cited

U.S. PATENT DOCUMENTS 3,848,569 A 11/1974 Folsom
6,458,585 B1 * 10/2002 Vachula ............... C12N 5/0639
435/405

(Continued)

FOREIGN PATENT DOCUMENTS

WO WO-9613573 A1 * 5/1996 ............ C12M 23/14
WO 03/010292 A2 2/2003
WO 2017/079674 A1 5/2017

OTHER PUBLICATIONS

Rosenblatt, J. et al., "Vaccination with dendritic cell/tumor fusion cells results in cellular and humoral antitumor immune responses in patients with multiple myeloma," Blood, 117(2):393-402 (Jan. 13, 2011).

(Continued)

*Primary Examiner* — Holly Kipouros
(74) *Attorney, Agent, or Firm* — Hamilton, Brook, Smith & Reynolds, P.C.

(57) ABSTRACT

Devices, systems, and methods can be used for the automated production of dendritic cells (DC) from dendritic cell progenitors, such as monocytes obtained from peripheral blood, and the automated generation of immunotherapeutic products from those dendritic cells, all within a closed system. The invention makes it possible to obtain sufficient quantities of a subject's own DC for use in preparing and characterizing vaccines, for activating and characterizing the activation state of the subject's immune response, and to aid in preventing and/or treating cancer or infectious disease.

17 Claims, 23 Drawing Sheets

Related U.S. Application Data continuation of application No. 15/970,664, filed on May 3, 2018, now Pat. No. 11,371,008, which is a continuation of application No. PCT/US2016/060701, filed on Nov. 4, 2016.

(60) Provisional application No. 62/250,618, filed on Nov. 4, 2015, provisional application No. 62/250,630, filed on Nov. 4, 2015.

(51) Int. Cl.
| | | |
|---|---|---|
| *A61K 40/19* | (2025.01) | |
| *A61K 40/24* | (2025.01) | |
| *A61K 40/45* | (2025.01) | |
| *C12M 1/00* | (2006.01) | |
| *C12M 1/02* | (2006.01) | |
| *C12M 1/26* | (2006.01) | |
| *C12M 1/42* | (2006.01) | |
| *C12M 3/06* | (2006.01) | |
| *C12N 5/0784* | (2010.01) | |

(52) U.S. Cl.
CPC .......... *A61K 40/24* (2025.01); *A61K 40/4524* (2025.01); *C12M 23/16* (2013.01); *C12M 23/28* (2013.01); *C12M 27/00* (2013.01); *C12M 29/04* (2013.01); *C12M 33/00* (2013.01); *C12M 35/08* (2013.01); *C12M 41/14* (2013.01); *C12N 5/0639* (2013.01); *C12N 2501/22* (2013.01); *C12N 2501/2306* (2013.01); *C12N 2501/25* (2013.01)

(56) References Cited

U.S. PATENT DOCUMENTS

| 11,371,008 | B2 | 6/2022 | Murthy |
|---|---|---|---|
| 11,767,500 | B2 | 9/2023 | Murthy |
| 2002/0041868 | A1 | 4/2002 | Nicolette et al. |
| 2004/0072347 | A1 | 4/2004 | Schuler et al. |
| 2005/0186669 | A1 | 8/2005 | Ho et al. |
| 2009/0155908 | A1 | 6/2009 | Halberstadt et al. |
| 2009/0162853 | A1 | 6/2009 | Clark et al. |
| 2011/0003380 | A1* | 1/2011 | Miltenyi ............... C12M 33/10 494/67 |
| 2011/0217690 | A1* | 9/2011 | Niazi ..................... C12M 23/58 435/3 |
| 2011/0250585 | A1* | 10/2011 | Ingber ................. B01L 3/50273 977/773 |
| 2012/0277652 | A1 | 11/2012 | Zhao |
| 2014/0322804 | A1 | 10/2014 | Boily et al. |
| 2015/0017716 | A1 | 1/2015 | Kauling et al. |
| 2015/0204767 | A1 | 7/2015 | Taniguchi |
| 2015/0368612 | A1* | 12/2015 | Palucka ............... A61K 31/675 435/325 |
| 2016/0178490 | A1 | 6/2016 | Civel et al. |
| 2017/0015965 | A1 | 1/2017 | Hata |
| 2017/0051238 | A1 | 2/2017 | Tanaka et al. |
| 2018/0251723 | A1 | 9/2018 | Murthy |
| 2022/0282200 | A1 | 9/2022 | Murthy |

OTHER PUBLICATIONS

Tuyaerts et al., "Generation of large Nos. of dendritic cells in a closed system using Cell Factories," Journal of Immunological Methods, 264: 135-151 (2002).

International Search Report and the Written Opinion of the International Searching Authority for International Application No. PCT/US2016/060701, titled: "Systems for Producing Cellular Immunotherapeutics and Methods of Use Thereof," Dated: Feb. 24, 2017 (12 pgs).

Notification Concerning Transmittal of International Preliminary Report on Patentability for International Application No. PCT/US2016/060701, titled "Systems for Producing Cellular Immunotherapeutics and Methods of Use Thereof," Dated: May 17, 2018 (7 pgs).

\* cited by examiner

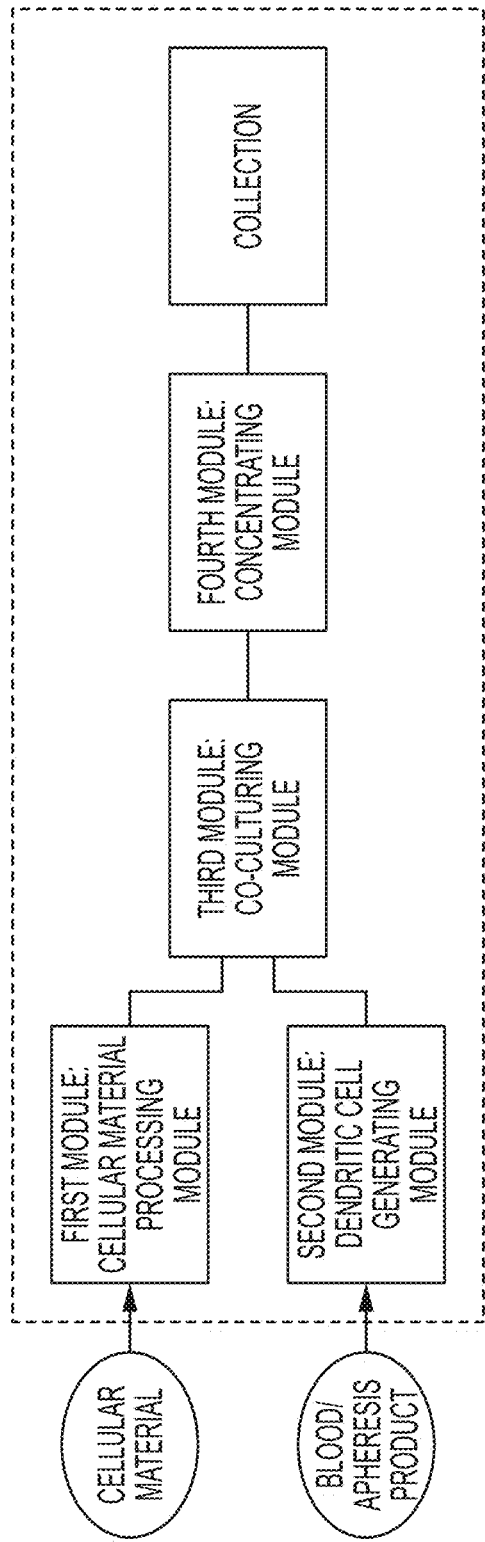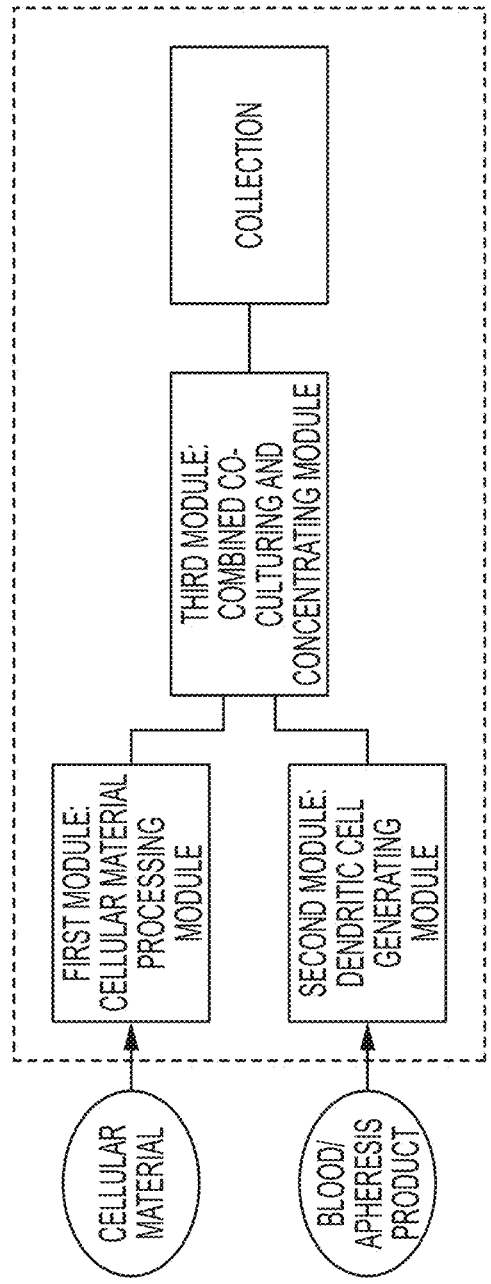

*IMMATURE DENDRITIC CELLS DEFINED AS LINEAGE 1 NEGATIVE AND HLA-DR POSITIVE

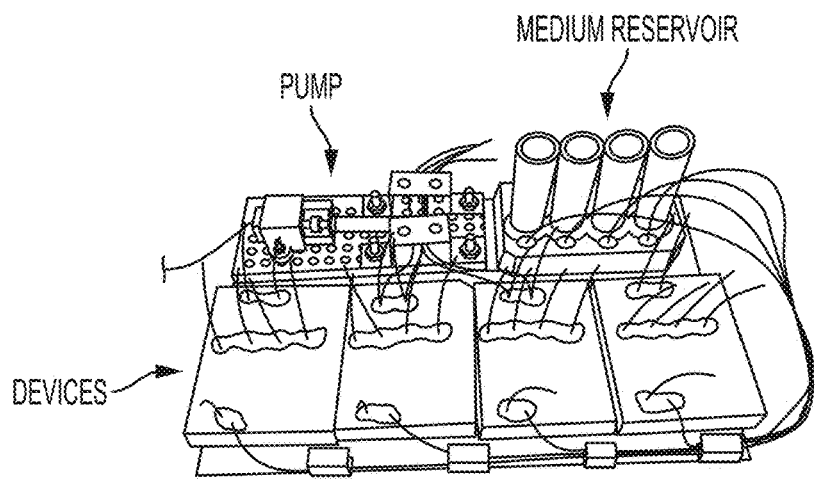
FIG. 11A
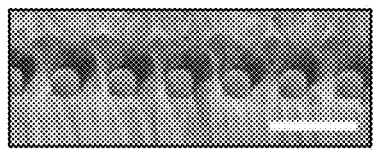
FIG. 11B(i)
FIG. 11B(ii)
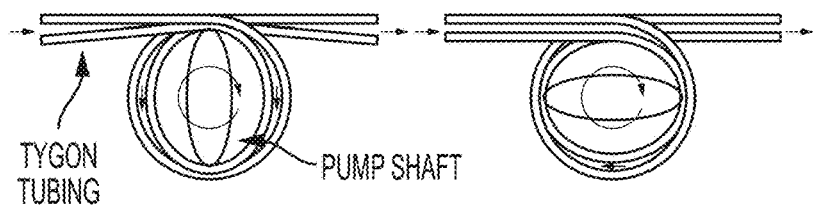
FIG. 11B(iii)
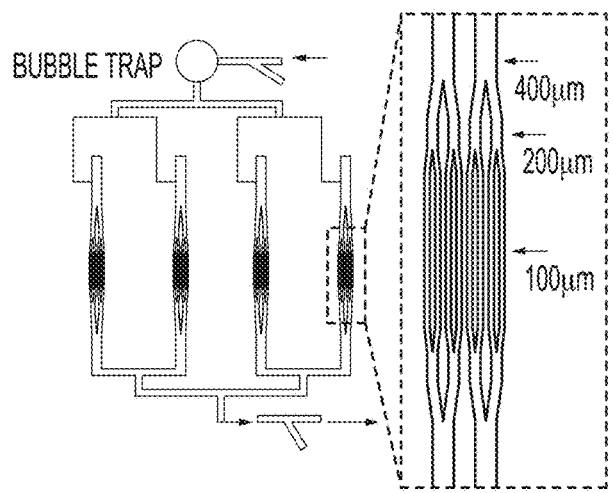
FIG. 11B(iv)

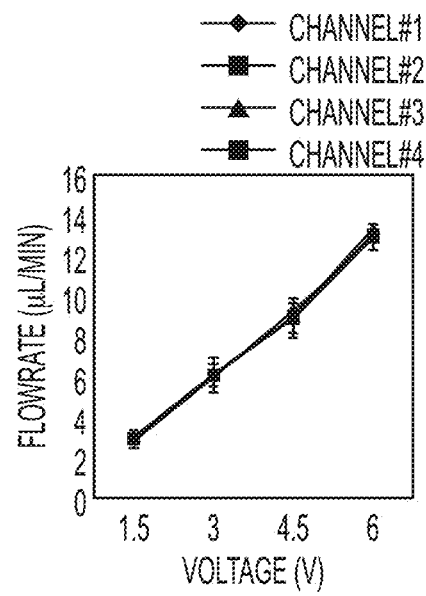
FIG. 11C(i)
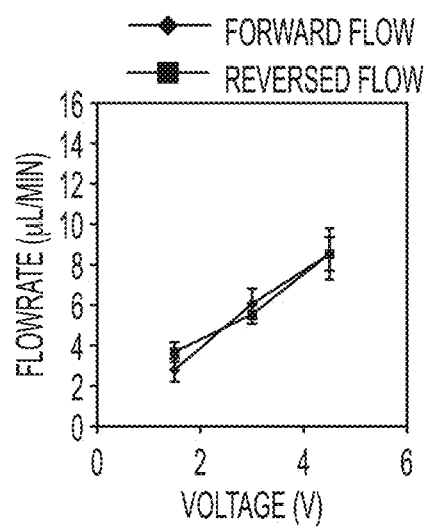
FIG. 11C(ii)
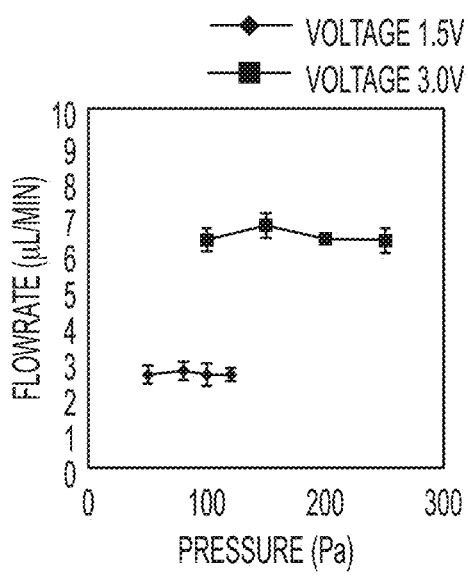
FIG. 11C(iii)
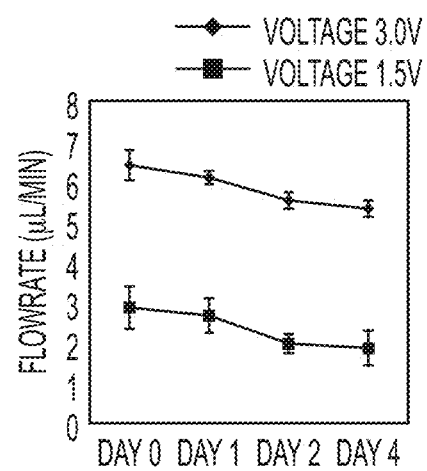
FIG. 11C(iv)

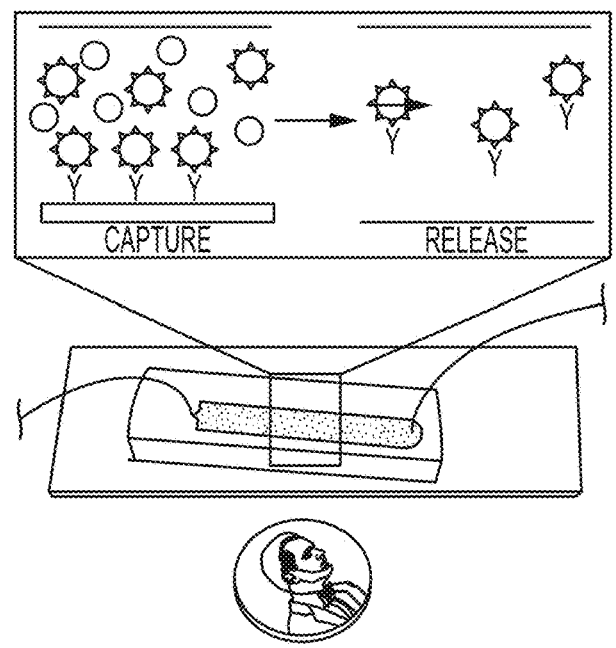
FIG. 13
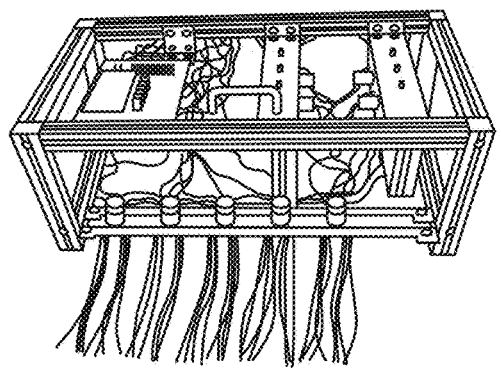
FIG. 14A
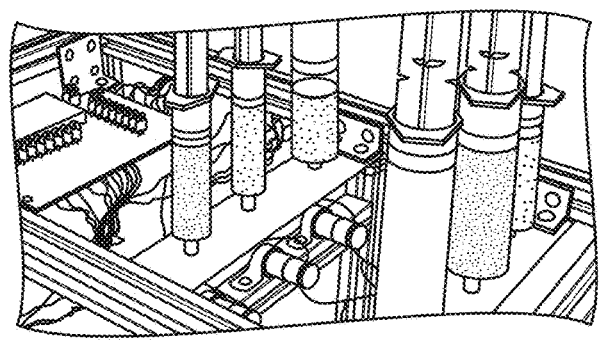
FIG. 14B
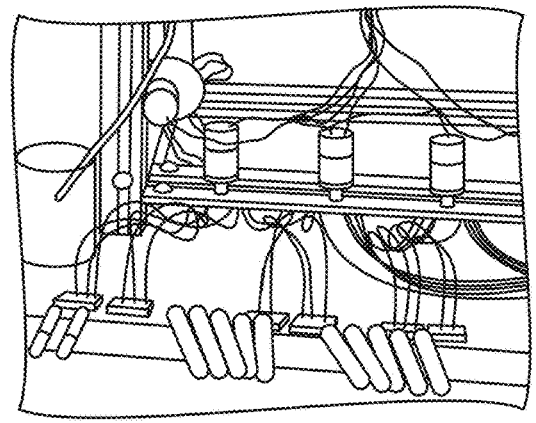
FIG. 14C

SYSTEMS FOR PRODUCING CELLULAR IMMUNOTHERAPEUTICS AND METHODS OF USE THEREOF

CROSS REFERENCE TO RELATED APPLICATIONS

This application is a continuation of U.S. application Ser. No. 17/664,532, filed on May 23, 2022, now U.S. Pat. No. 11,767,500, issued on Sep. 26, 2023, which is a continuation of U.S. application Ser. No. 15/970,664, filed on May 3, 2018, now U.S. Pat. No. 11,371,008, issued on Jun. 28, 2022, which is a continuation of International Application No. PCT/US2016/060701, which designated the United States and was filed on Nov. 4, 2016, published in English, and which claims the benefit of and priority to U.S. Provisional Application No. 62/250,630, filed on Nov. 4, 2015, and U.S. Provisional Application No. 62/250,618, filed on Nov. 4, 2015. The entire teachings of the above applications are incorporated herein by reference.

GOVERNMENT SUPPORT

The invention was made with government support under contract number NU24 AI118665 awarded by National Institutes of Health. The government has certain rights in the invention.

FIELD OF THE INVENTION

The invention generally relates to systems for producing immunotherapeutic products and methods of use thereof.

BACKGROUND

Cancer immunotherapy is an area of extraordinarily high activity in academic science, big pharma, and venture-backed pharma. This area has received a lot of attention based on extraordinary promising treatments for leukemia based on chimeric antigen receptor T cell (CAR-T) therapy and the recent successes for clinical-stage companies developing new cellular immunotherapies. Indeed, this area of medicine also has its own Exchange Traded Fund (ETF), the Loncar Cancer Immunotherapy Index (ETF) whose 30 or so different constituent companies have a collective market capitalization of over $30B.

An important sub-area in this field is that of the dendritic cell (DC) vaccine. Unlike CAR-T therapies which have as yet only a limited set of targets, DC vaccines can be designed not only to target an unlimited number of tumor antigens but also act as a continuous, real-time monitor within the body against tumor relapse as well as new tumors whose genomic signature may be different from that of the original tumor. DC vaccines are prepared using an intensive manual process as shown in FIG. 1. That is, all of the steps are carried out manually using standard cell culture techniques, in single-plex form. The manual approach is highly dependent on the skill level of the operator and, even with significant training, product yields and quality can vary.

The manual approach can be satisfactory for small companies at the Phase I clinical trial level, as well as in academic environments where labor costs (e.g., technicians/graduate students/postdocs) are low and patient numbers are below 20-30 individuals. However a number of DC vaccines are entering Phase III clinical trials and in these studies the number of patients can be on the order of about 500 individuals scattered across multiple clinical sites throughout the U.S. Vaccine production in such situations cannot be performed in a completely manual, single-plex manner. Thus, there exists a need to develop new technology to automate the production of DC vaccines.

SUMMARY

The invention provides self-contained and fully automated fluidic systems for manufacture of cell-based immunotherapeutic products, replacing the currently used manual protocol with an automated method for culturing and generating immunotherapeutic products, such as dendritic cell (DC) vaccines for cancer immunotherapy. The conceptual basis for this process is to obtain dendritic cells from a patient, and expose these cells to key components of the patient's tumor (components can be whole tumor cells, peptides expressed by the tumor, or tumor nucleic acids) such that when returned to the patient's body, these cells mobilize the patient's own immune system in a manner that targets the patient's tumor.

The systems of the invention accept tumor material and patient blood (or apheresis product) and carry out all of the subsequent steps, as outlined in FIG. 2, without the need for manual intervention, to provide a cell-based immunotherapeutic that can be directly infused into the patient. The only inputs needed with this self-contained, or "closed" system, are patient blood/apheresis/leukapheresis product and tumor material. The remainder of the steps takes place without additional input and provides as output the cellular therapeutic products that are entirely ready for infusion into the patient. In this way, the risks of contamination are greatly decreased and the robustness and reproducibility of the manufacturing technique are greatly increased, both key considerations for safe and reliable manufacturing of therapeutic products. Within this system, the ability to remove samples for testing without introducing new material or contaminants is also provided. A general overview of the method as carried out using the closed systems of the invention is provided in FIGS. 2-3. As shown, the system has various component instrumentation, such as a cell selection module (e.g., cellular material processing module) and a cell culture module (e.g., co-culturing module), automated flow control, and a number of reservoirs for reagents and waste.

Briefly, the steps in production of the cellular therapeutic product consist of purifying monocytes from the blood/apheresis/leukapheresis product, conversion of these monocytes into dendritic cells, stimulation of these dendritic cells with tumor material taken from the same individual, along with multiple wash and material transfer steps.

Beyond simplifying and potentially shortening the process of generating DCs and immunotherapeutic products, the fluidic systems of the invention significantly improve the utilization of patient blood and tumor samples for cell-based therapies, reliability and robustness of the manufacturing process, along with cost reductions (e.g. labor costs). Furthermore, methods are readily scalable from the processing of 1-10 patient samples to 100s of patient samples. Specifically, the fluidic system is a fluidic network of channels and chambers that are perfused by pumps that are optionally mounted directly on one or more chips, or modules. This configuration enables automated fluid flow control to bring cultured cells in contact with monocyte-to-DC conversion reagents as well as to bring DCs generated within the system in contact with cellular material that expresses an antigen, such as tumor material. This design is also easily scalable. For example, by designing a system with a series of modules arranged in parallel, a single system can process samples ranging from 1-10 to 100s of samples. In comparison to conventional fluidic chips coupled to large syringe pumps, each chip, or module, can be independently controlled and the number of chips utilized at any given time can be scaled up or down depending on the number of samples. In other embodiments, a single central controller, such as a PLC logic controller, controls all of the modules in the system.

An exemplary arrangement is now described in which systems and methods of the invention utilize modules that are fluidically coupled to one another for carrying out various aspects of processing a patient's blood and tumor samples to produce an immunotherapeutic. The skilled artisan will appreciate that is an exemplary arrangement of the fluidic modules described herein and that other arrangements are within the scope of the invention. Such arrangement will be based on the output desired to be produced.

In this exemplary embodiment, a first module is used to receive and/or process cellular material, such as a tumor sample from the patient (e.g., needle biopsy, solid tissue, cells, cellular components released from cells such as proteins or nucleic acids). A second module is used to receive a patient sample, such as blood or plasma sample. The blood or plasma sample includes monocytes (MCs). The second module is configured to generate dendritic cells from the monocytes in the sample. Subsequently, the processed cellular material and generated dendritic cells are combined and co-cultured in a third module to produce an immunotherapeutic product. The systems and methods are designed such that any number of additional modules for carrying out any number of processes can be provided. The systems are also designed to be housed within an incubator. Alternatively, the systems of the invention can include onboard heating elements.

In certain aspects, the invention provides systems for producing a cell-based immunotherapeutic products, two embodiments of which are generally shown in FIGS. 4A and 4B, that includes a first module for processing cellular material associated with a disease of a patient, a second module for generating dendritic cells, and a third module for co-culturing the processed cellular material and the generated dendritic cells to produce an immunotherapeutic. The third module is in fluidic communication with the first and second modules so that it receives a flow of processed cellular material from the first module and a flow of generated dendritic cells from the second module.

In another aspect, the second module includes a cell culture chamber having a monocyte-binding substrate, a fluid inlet port, and a fluid outlet port in fluidic communication with the third module. The fluid inlet port and the fluid outlet port are fluidically coupled to the cell culture chamber to provide a flow of a liquid culture medium across the substrate. The fluid inlet port and the fluid outlet port are disposed at opposite ends of the chamber. With respect to the monocyte-binding substrate, the substrate forms a bottom of the cell culture chamber and has a flat surface. The substrate can alternatively be designed such that monocytes bind to surfaces that are not flat, as shown in FIG. 16B. In certain aspects, the surface of the monocyte-binding material binds to monocytes but not to other differentiated blood-derived cells.

In some embodiments, the system includes a fourth module for concentrating the immunotherapeutic, as shown in FIG. 4A. The fourth module is coupled to an outlet of the third module. In some aspects, the fourth module is a flow-through chamber. In other aspects, the fourth module has a filter for filtering out material other than the immunotherapeutic. In yet other aspects, the fourth module has a fluid inlet for the introduction of wash fluid. It is to be understood that, in other embodiment, the immunotherapeutic is instead concentrated in the third module, as shown in FIG. 4B.

In certain aspects, at least part of the system comprises disposable components, some or all of which can be housed within a non-disposable frame. In other aspects, all components of the system are disposable. Furthermore, in some embodiments, the system includes a sample tracking component for tracking and documenting patient material.

In another aspect of the invention, a method for generating cell-based immunotherapeutic products is provided. Generally, the method includes the steps of providing cellular material associated with a disease from a patient in a first module of the fluidic system, generating dendritic cells from monocytes of a patient sample in a second module of the fluidic system, flowing processed cellular material from the first module and generated dendritic cells from the second module into a third module of the system, and co-culturing the processed cellular material and generated dendritic cells in the third module to produce an immunotherapeutic.

The cellular material provided to the first module can include a fine needle aspirate of cancerous material and a solid tumor tissue. In certain aspects, the first module processes the solid tumor tissue. Some aspects of the invention, the first module breaks down the solid tumor tissue into individual cells and/or releases the internal contents of the cells. Exemplary internal contents include proteins, peptides, nucleic acids, and combinations thereof.

In some aspects, methods of the invention further involve concentrating the immunotherapeutic in a fourth module, the fourth module being in fluidic communication with the third module. In yet other aspects, methods of the invention involve concentrating the immunotherapeutic in the third module. After processing in the modules is complete, methods of the invention involve collecting the immunotherapeutic for immediate delivery to a patient or to be stored for later use.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 4A and 4B are schematics depicting systems of the invention in two embodiments.

FIGS. 11A-D shows system setup and characterization where (A) shows an image of the chip-based cell culture platform with the pump contained within the chip. (B(i)) shows a cross-sectional view of the circular-cross section micro-channels. Scale bar, 300 µm. (B(ii)) shows a magnified view of the tubing coil within the PDMS block. (B(iii)) Schematic diagram illustrating the turning of the pump shaft as it locally compresses the tubing and drives fluid flow. (B(iv)) shows a schematic diagram of the fluidic channels which are grouped as four channels with four such groups connecting to a single bubble trap. The chip shown in (A) contains a total of sixteen such groups connected to four bubble traps. (C(i)) shows the flow rate measurement of the four independent flow circuits through the four fluidic devices, n=3. (C(ii)) shows the flow rate measurement of the miniaturized pump determined via particle image velocimetry (PIV) in both forward and reversed flow direction. (C(iii)) shows pump stability under various pressures, n=3. (C(iv)) shows stability of the pump over a 4 day period, n=3. (D) shows schematic layout of the device operation for cell injection, cell culturing, and perfusion assay.

FIG. 13 shows exemplary microfluidic devices coated with degradable hydrogels containing antibodies for selective capture of target cells from whole blood and non-destructive release under mild conditions.

FIGS. 14A-14E show an automated fluid injector system pumping pump 6 different kinds of aqueous solutions into 48 fluidic devices. An additional pressure-based pumping system was included to pump viscous hydrogel solutions into the devices. (A) photograph of the automated system that would typically be connected to a gas cylinder and laptop. (B) fluid reservoirs. (C) the white tubing seen in (A) connected to individual fluidic chips. (D) system diagram showing channel and pumping layouts. (E) an image of a home-built LabView program that allowed specification of incubation times for each fluid type along with flow rates for the aqueous pumping system and the hydrogel pumping system.

FIG. 16C shows heat maps for the top most altered genes after BCG re-stimulation comparing pre-vaccination and day 56 post-vaccination (memory/effector responses), for PO and ID BCG groups separately. The Venn diagram comparing the unique gene lists identified on day 56 post-vaccination (FIG. 16D) demonstrates that PO and ID BCG induced distinct memory patterns. Preliminary GSEA analysis indicated that a set of asthma-associated genes were enriched in PO BCG recipients at both day 7 and 56.

Figure 16A:
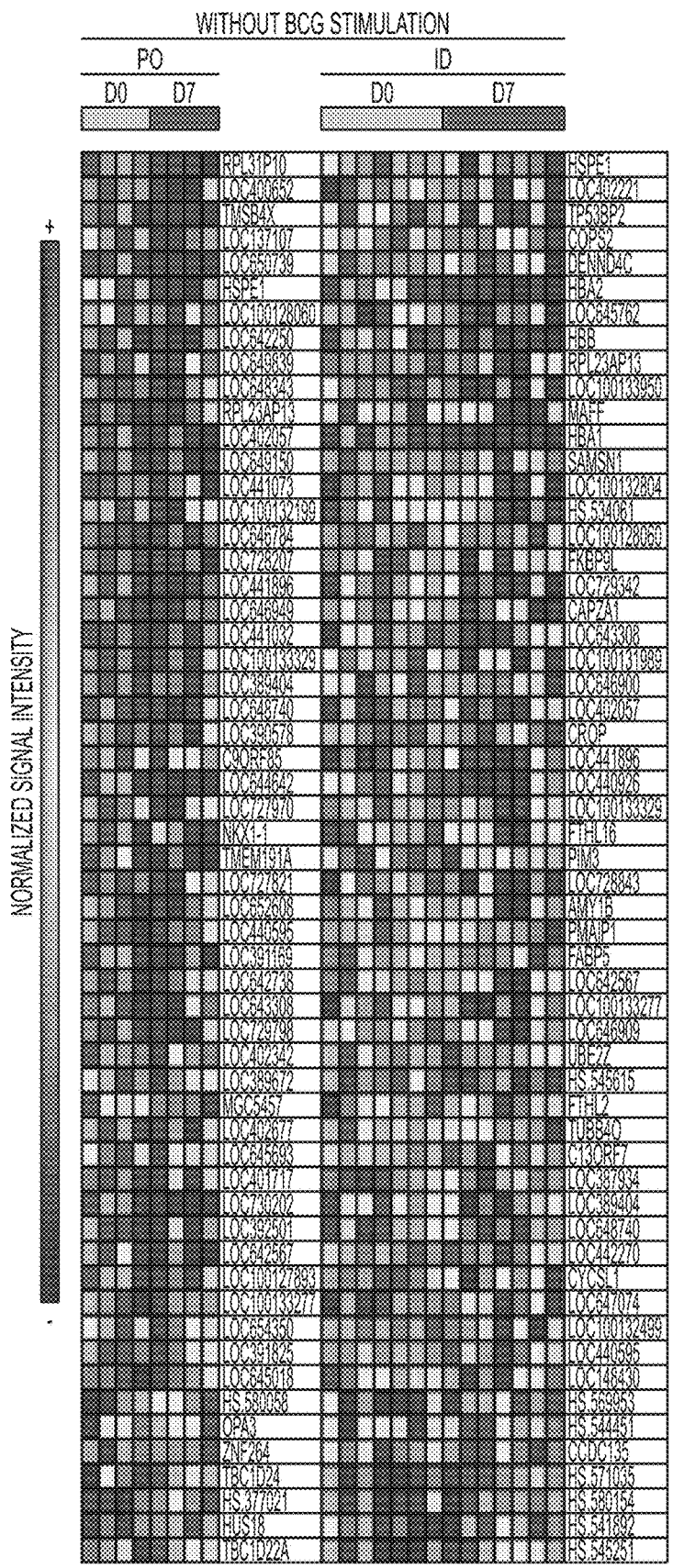
FIGS. 16A-16D shows heat maps for the top most altered genes directly ex vivo comparing pre-vaccination and day 7 post-vaccination (peak of T cell activation) responses, for PO and ID BCG groups separately. BCG vaccination reproducibly altered expression patterns similarly across individuals within each group. The Venn diagram comparing the unique gene lists identified on day 7 post-vaccination (FIG. 16B), demonstrates that PO and ID BCG induced distinct activation patterns.
Figure 16A:
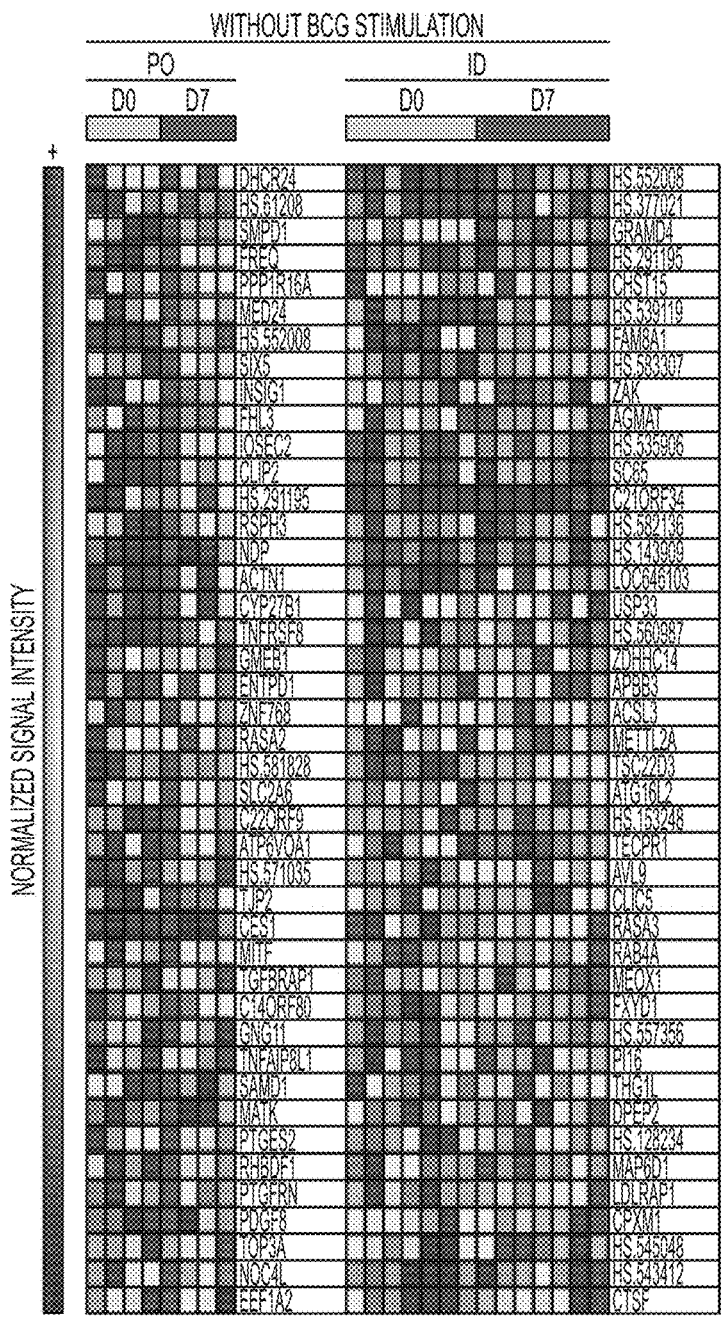
Figure 16B:
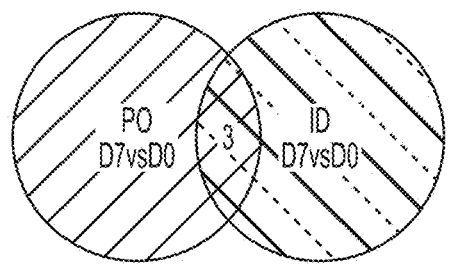
Figure 16C:
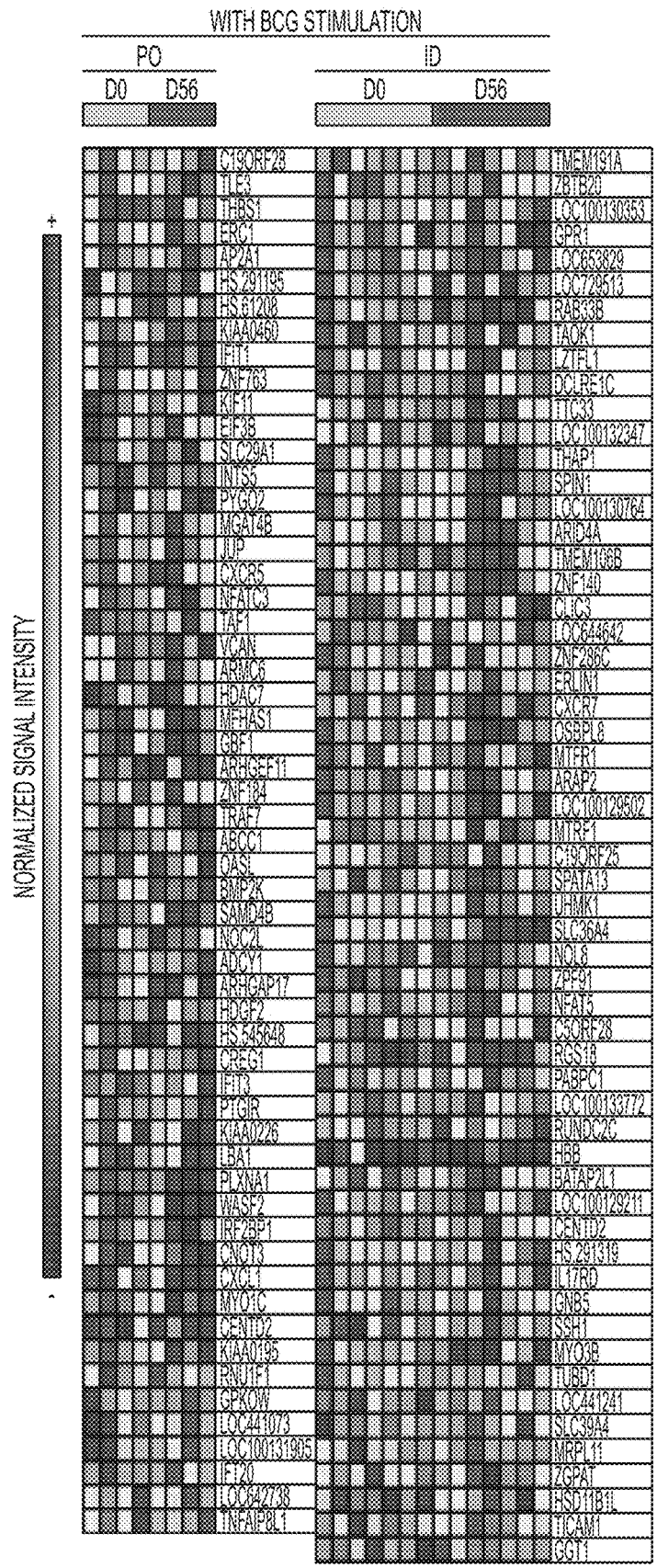
Figure 16C:
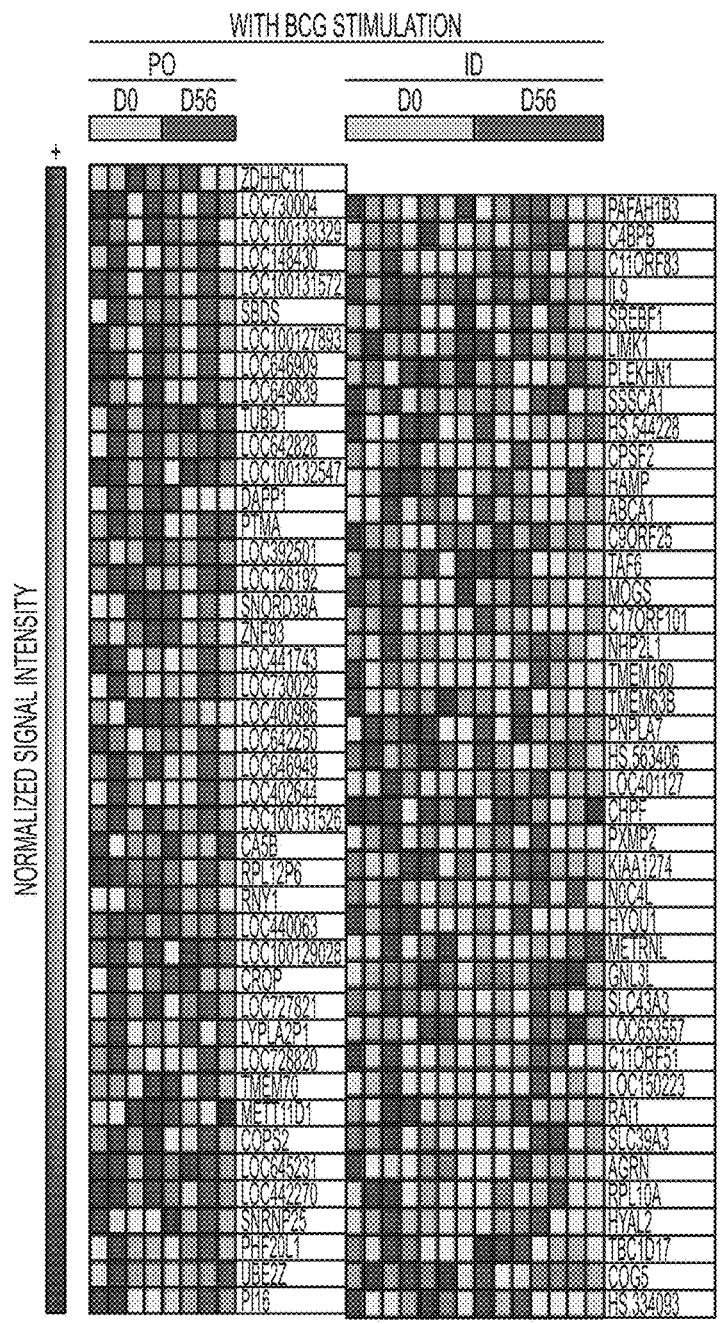
Figure 16D:
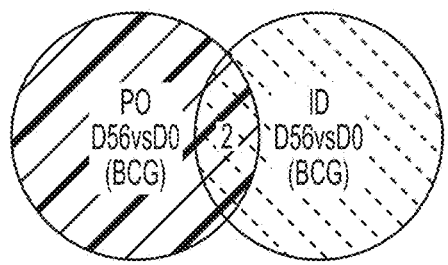

Distinct T cell Molecular Signatures are Induced by PO and 1D BCG vaccination. Heat maps (FIG. 16A & FIG. 16C) showing the top 100 most altered genes identified comparing pre-(D0) and post-BCG (D7 in FIG. 16A, and D56 in FIG. 16C) responses, direct ex vivo (FIG. 16A) or after BCG re-stimulation (FIG. 16C). Each individual column represents a single individual's responses clearly demonstrating these gene lists were reproducibly altered across subject groups. Signal intensities (i.e. gene expression levels) are illustrated by varying shades of red (increases) and blue (decreases). The Venn Diagrams (FIG. 16B and FIG. 16D) compare altered gene lists detected in PO and ID vaccinated groups on day 7 directly ex vivo (FIG. 16B) or day 56 after BCG re-stimulation (FIG. 16D). Post-vaccination PO and ID signatures were predominantly distinct.

Figure 17:
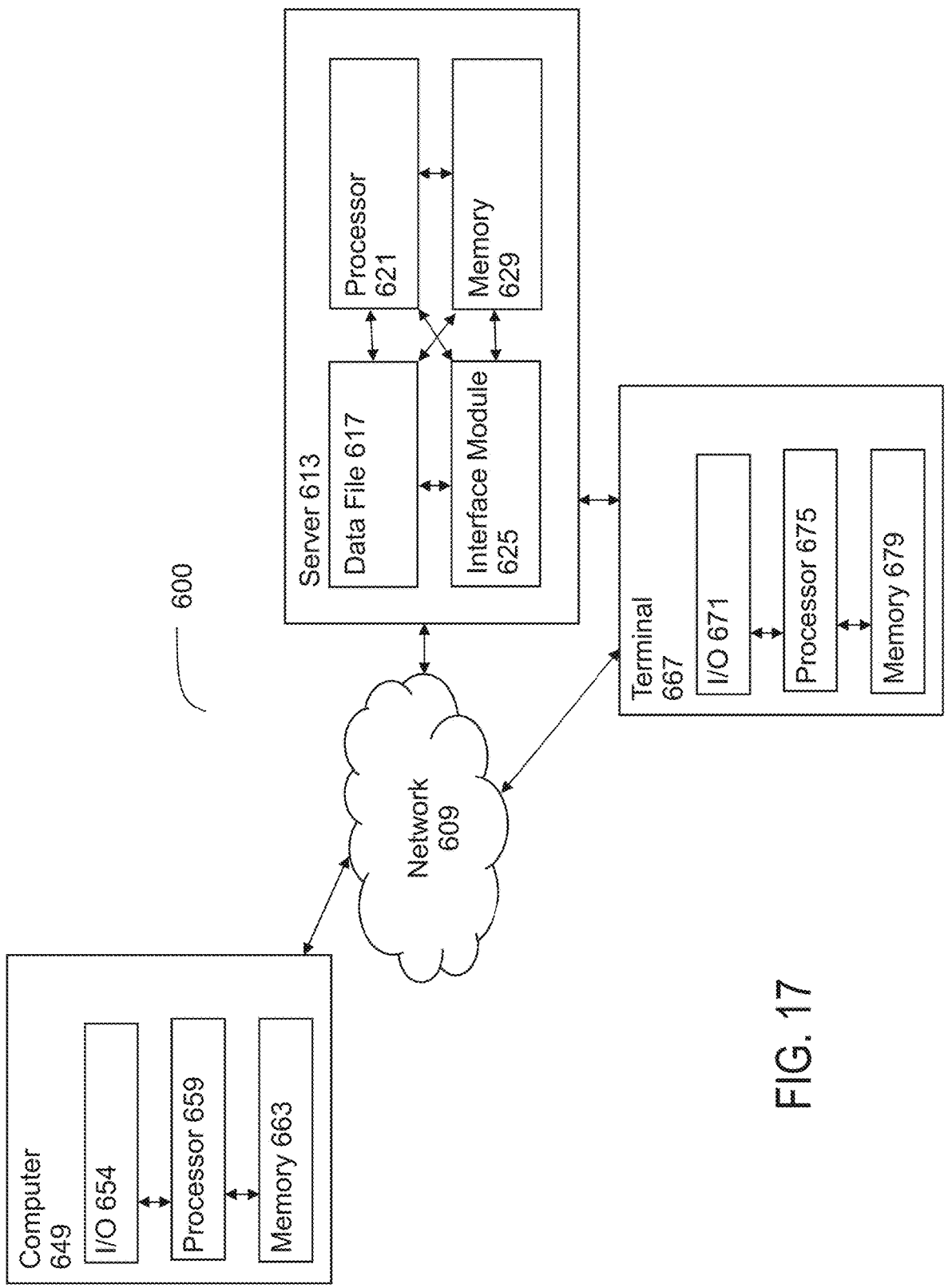

FIG. 17 shows a system according to the invention.

DETAILED DESCRIPTION

Devices, systems, and methods can be used for the automated production of dendritic cells (DC) from dendritic cell progenitors, such as monocytes obtained from peripheral blood, and the automated generation of immunotherapeutic products from those dendritic cells, all within a closed system. The invention makes it possible to obtain sufficient quantities of a subject's own DCs for use in preparing and characterizing vaccines, for activating and characterizing the activation state of the subject's immune response, and to aid in preventing and/or treating cancer or infectious disease.

The invention makes it possible to automate as well as to remotely monitor and control methods of DC differentiation and maturation as well as the co-culturing of DCs and non-dendritic cellular material. The methods, devices, and systems of the invention can be scaled up to provide a large number of DCs and cell-based immunotherapeutic products, and can be operated either for a single subject or for several subjects in parallel (whereby their cells and the progeny thereof remain separate). In accordance with the invention, the immunotherapeutic product can be an antibody-based immunotherapeutic product or a cellular-based immunotherapeutic product. Anti-body based immunotherapeutic products are immunotherapeutic products that are comprised of one or more antibodies, wherein cellular-based immunotherapeutic products are immunotherapeutic products that are comprised of cellular materials (e.g., human cells). In a preferred embodiment, the immunotherapeutic product is a cellular-based immunotherapeutic product. Compared to prior art methods and devices, the methods and devices of the invention are robust in their operation, capable of providing high product yields, simple and efficient, and reduce the costs of expensive reagents (e.g., cell culture media and cytokines) to a minimum.

The invention makes available a ready supply of a patient's DCs combined with non-dendritic cellular material, such as material that expresses a cell-surface antigen (cancer antigens), to produce cell-based immunotherapeutic products, which have many uses. For example, the products can be used to produce customized DC-based vaccines for combatting cancer or infectious disease of the patient. DC vaccines can be designed not only to target an unlimited number of tumor antigens but also act as a continuous, real-time monitor within the body against tumor relapse as well as new tumors whose genomic signature may be different from that of the original tumor. A patient's DCs also can be used to provide a supply of activated DCs suitable for introduction into the patient. The patient's DCs can be activated in vitro by exposure to one or more antigens, and the activated DCs can be used to activate T cells of the patient, either in vitro or by introducing the activated DCs into the patient.

In the present invention, key components of the patient's tumor (components can be whole tumor cells, peptides expressed by the tumor, or tumor nucleic acids) are introduced to the DCs to produce cell-based immunotherapeutic products, such that when the immunotherapeutic products are returned to the patient's body, these cells mobilize the patient's own T cells in a manner that targets the patient's tumor. Thus, the immunotherapeutic products produced by the invention can be used to improve vaccine development. Furthermore, DC vaccines can be designed not only to target an unlimited number of tumor antigens but also act as a continuous, real-time monitor within the body against tumor relapse as well as new tumors whose genomic signature may be different from that of the original tumor.

Figure 1:
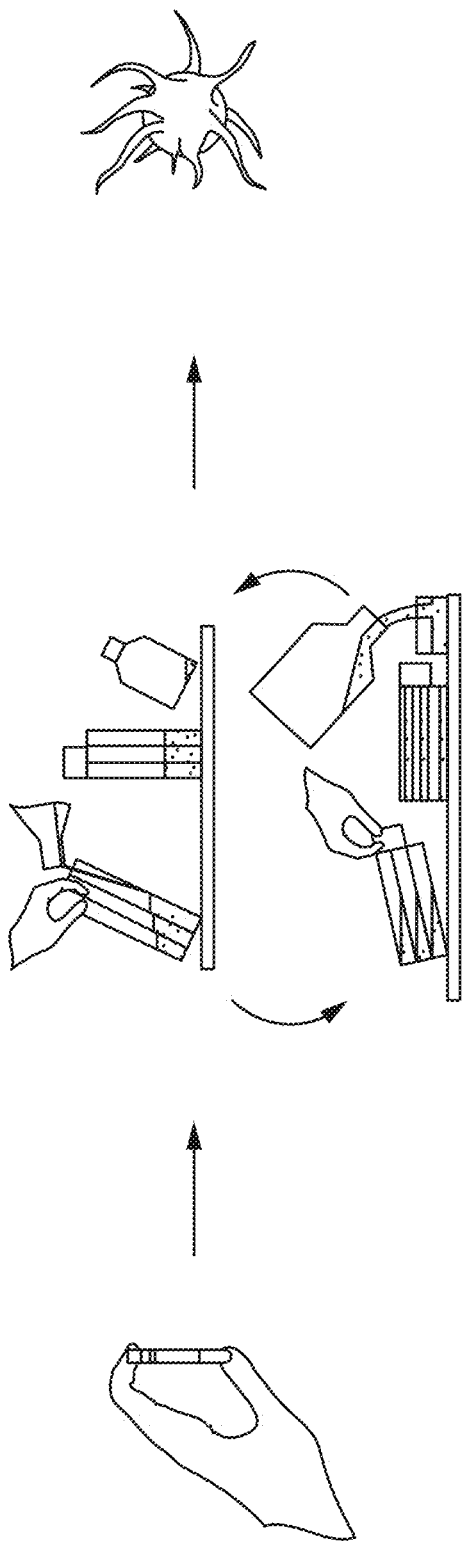
FIG. 1 shows a prior art manual technique for producing immunotherapeutic products.
Figure 2:
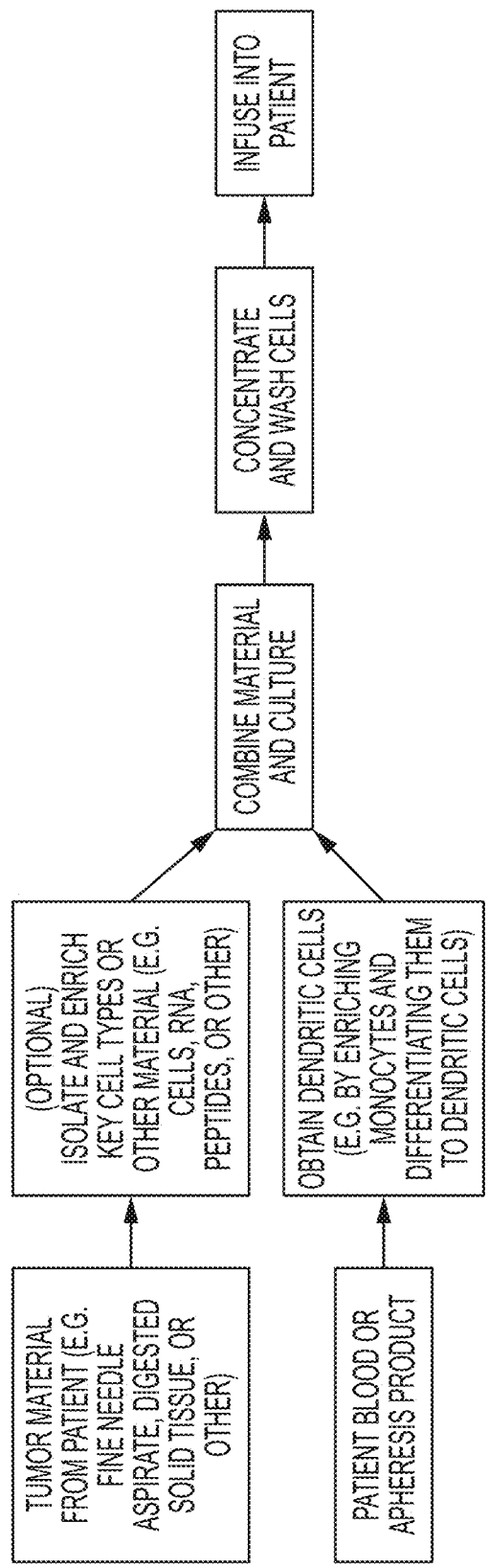
FIG. 2 is a flow chart showing the steps for producing immunotherapeutic products.
Figure 3:
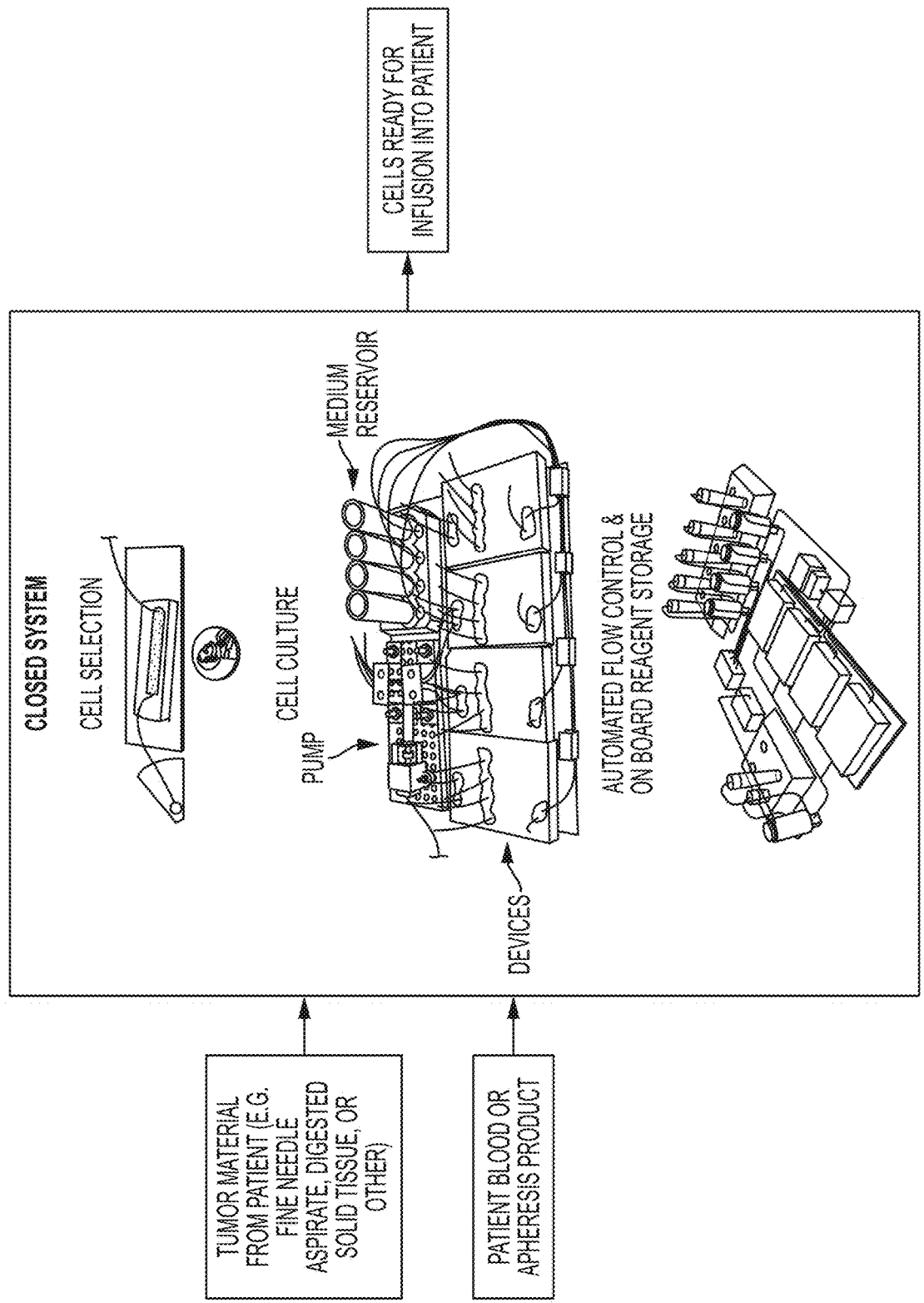
FIG. 3 is a flow chart showing an embodiment of a method of the present invention for producing immunotherapeutic products.

The method of generating cell-based immunotherapeutic products of the present invention is far simpler and more efficient than methods of the prior art. FIG. 1 shows the manual prior art technique that requires at least 16 manual and labor intensive steps. In contrast, FIGS. 2-3 show an overview of a method for generation of cell-based immunotherapeutic products using the systems described herein.

Systems and methods of the invention utilize modules (e.g., cassettes) that are fluidically coupled to one another for carrying out various aspects of processing a patient's blood and tumor samples to produce an immunotherapeutic product. The systems include a combination of modules that are interchangeable in terms of channel dimension, flow geometry, and interconnections between the different functional parts of the devices. Each module is designed for a specific function, such as dendritic cell generation and culturing of dendritic cells and tumor material, all of which are integrated to provide a cell-based immunotherapeutic product. The microfluidic modules are designed, chosen, and arranged based on the particular immunotherapeutic product to be generated.

By nature of flow-processes, each module in the platforms of the invention is exceptionally scalable, whereby modules can be added in parallel by numbering up the constitutive units in order to increase throughput. Additionally, stacks of processing units, of various sizes and configuration, can be combined together to produce immunotherapeutic products. The system is also equipped with numerous classes of software, such as an advanced real-time process monitoring and control algorithm, allowing for feedback control, as well as algorithms that allow integration and scale-up given reaction and purification results obtained using the system.

In an exemplary embodiment, the system includes a combination of micro-, or macro-fluidic modules (chips) and tubing with interchangeable modules in terms of channel dimensions, flow geometry, and inter-connections between the different functional parts of the devices. Each module and tubing is designed for a specific function, such as tissue processing, dendritic cell generation, cell culturing, concentration, and purification, all integrated for the continuous manufacturing of an immunotherapeutic product. Both homogenous and heterogeneous processes are considered which are suitable for flow application. These processes are designed and optimized with respect to the starting materials and operating conditions, such as temperature, pressure and flow rates so as to not readily clog the system during the flow process.

As a result, the systems and methods of the invention represent a revolution from a manual process towards personalized continuous manufacturing platform that provides for real time implementation in manufacturing facilities, hospitals and emergency locations. Systems and methods of the invention bring a competitive advantage in not only the quality and economics of the immunotherapeutic products produced, but also the flexibility and agility for real-time production to overcome development, manufacturing, and supply chain challenges.

Each functional part of the device may include a module or tubing connected to a set of actuators, including valves, flow controllers, pumps, etc., sensors, such as flow rate sensor, pressure sensor, thermocouple, and heat transfer elements, including but not limited to a Peltier element, and reservoirs. The reservoirs may collectively act as buffer elements between the different steps to seamlessly connect the processes, which have various volumetric throughputs, such that continuous flow may be achieved throughout the device (although discontinuous flow/stop flow, may also be used within the systems and methods of the invention). The materials of equipment are chosen with the appropriate chemical compatibility under different temperature and pressure rating specific to each process. Additionally, the choice of pumps implemented in the device, such as syringe, peristaltic and rotary pump, ranges from a nL to a mL in flow rates and 10 to 10,000 psi in pressure depending on the flow and pressure requirements for the different functions. At least one, and sometimes a plurality or all steps during the manufacturing process are monitored for product characteristics (e.g. purity forms) using a variety of inline process analytical tools (PAT) or miniaturized micro-total analysis system (micro-TAS), such as laser light scattering, UV/Vis photodetector, chromatography, and, more recently, mass spectrometry and Raman spectroscopy.

The method of device scale-up is performed by parallel addition of module reactors or enlargement of the module channels while maintaining a set of dimensionless parameters characteristic to each process constant and dimensional parameters within the upper and lower bound limit. During process integration and optimization, the process decision variables, including temperature, pressure, flow-rate and channel dimensions, are varied to achieve the desired trade-off between yield, purity and throughput. Throughout the optimization process, the aforementioned set of dimensionless parameters undergo an algebraic optimization with operational constraints. The operational constraints are the lower and upper bound of the decision variables. The objective function considers a combination of purity, yield and throughput operating variables. While the dimensionless parameters determine the steady-state quality of the device, the start-up quality of the device is also important as it determines the time required to reach steady state and, in turn, the productivity of the device in the form of lag-time and waste. The start-up dynamics are analyzed using both simulation and experimentation, the results of which are used to perform a start-up optimization by implementation of real-time feedback control.

The inner dimensions of any module's channel may range from the micrometer to the millimeter. The throughput of the device can be as low as 10 nL/min and as high as 1 mL/min. For a lower throughput, a chip-based module device may be used using transparent materials with the appropriate chemical compatibility and pressure and temperature rating. For a higher throughput, a tube-based module device may be used with the same requirements. Any module may be temperature-controlled using, for example, a peltier-coupled with a liquid-bath while the module tube is coiled around a conducting cylindrical platform, temperature-controlled using a ministat.

The invention represents an upgrade in immunotherapeutic product manufacturing, providing flow-based immunotherapeutic production technology with an unparalleled degree of consistency, economy, scalability, flexibility, and portability. The fluidic-based systems and methods of the invention in turn address the following key issues associated with current immunotherapeutic product development and manufacturing processes.

Inconsistent and uneconomical immunotherapeutic product manufacturing using current manual or batch production technologies are overcome. Design changes associated with scale up during different stages of immunotherapeutic product development is addressed. In current immunotherapeutic product development process, engineering knowledge, gleaned from bench- and pilot-scale experiments, does not directly translate to manufacturing scale due to scale-up nonlinearities, such as shear, mixing, and heat transfer phenomena. A further complication is that different scale up criteria cannot be met simultaneously.

An exemplary system for producing an immunotherapeutic product is now described. The skilled artisan will appreciate that this exemplary combination of modules is based on scale and the desired output as well as the product to be produced. Scale-up of this exemplary embodiment will be within the knowledge of skilled artisan by adding modules to allow for parallel processing. The skilled artisan will also appreciate that different or alternative module arrangement may be desired based on the product to be produced.

In this exemplary embodiment, a first module (cellular material processing module) is used to receive and/or process cellular material, such as a tumor sample from the patient. A second module (dendritic cell generation module) is used to receive a patient sample, such as blood and generate dendritic cells from the monocytes in the sample. In one embodiment, both the cellular material and the DCs are obtained from a single individual. In another embodiment, the cellular material and the DCs are obtained from different individuals of the same species (e.g. *Homo sapiens*). Subsequently, the processed cellular material and generated dendritic cells are combined and co-cultured in a third module (co-culturing module) to produce a cell-based immunotherapeutic product. In some aspects, a fourth module is also provided for concentrating and washing the cell-based products (concentration module). The systems and methods are designed such that any number of additional modules for carrying out any number of processes can be provided. The systems are also designed to be housed within an incubator. Additional detail regarding each of these modules, as shown in FIGS. 4A and 4B, will now be described.

Dendritic Cell Generating Module

Figure 5:
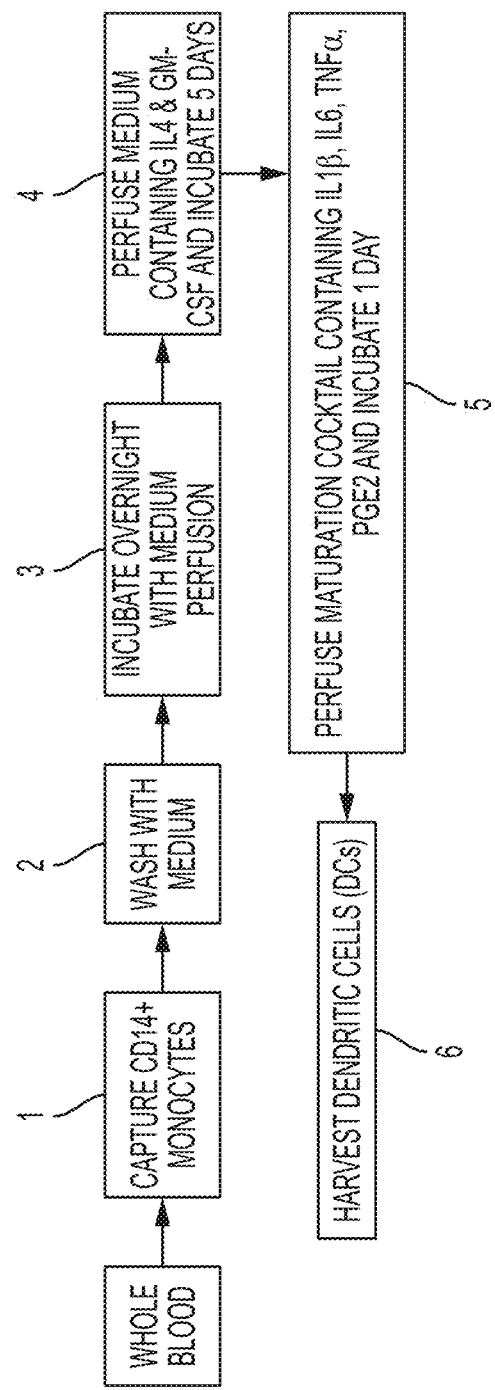
FIG. 5 is a flow chart showing an embodiment of a method of the present invention for generating dendritic cells within the second module.
Figure 6A:
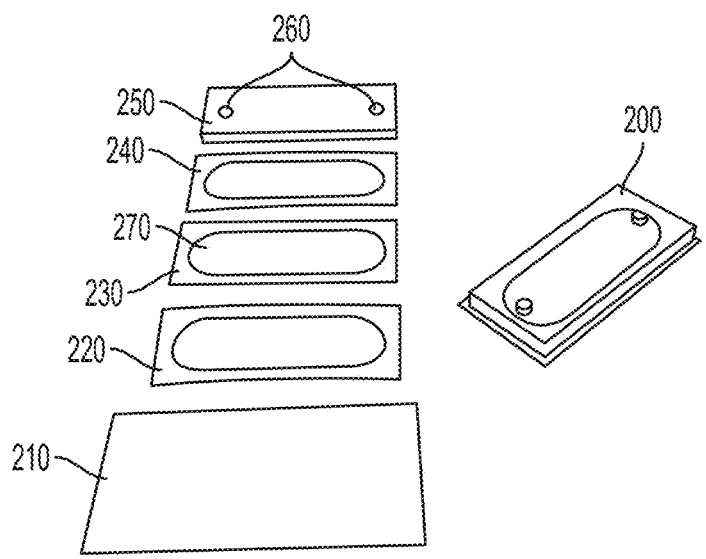
FIG. 6A left hand side, is an illustration of the individual parts used to prepare a dendritic cell differentiation cassette of the present invention. The assembled dendritic cell differentiation cassette is shown at the right-hand side of FIG. 2A.

In one aspect of the present invention, monocytes (MC) are isolated from circulating blood of a subject and converted into dendritic cells (DC) using the dendritic cell generating module. Such an exemplary module is described in PCT/US2016/040042, the content of which is incorporated by reference herein in its entirety. FIG. 6A shows a preferred design of a dendritic cell generation module as provided in the system. The dendritic cell generating module generally includes a cell culture chamber comprising a monocyte-binding substrate, a fluid inlet port, and a fluid outlet port in communication with the co-culturing module (described in more detail below). In one aspect, the fluid inlet port and the fluid outlet port are fluidically coupled to the cell culture chamber, such that a liquid culture medium flows from the inlet port, across the substrate, and to the outlet port. The process for generating dendritic cells from monocytes within the second module is shown in FIG. 5.

More specifically, dendritic cell generating module 200 is built from the layers shown at the left side of the FIG. 6A, which are assembled with the aid of double-sided adhesive film. The design of the module allows it to receive a suitable volume of whole blood or another fluid sample containing MC, binding essentially all of the MC contained in the sample. The cassette contains a cell culture chamber 270 which forms the central open fluid space within the cassette. The floor of the chamber is, or contains as a portion thereof, an MC binding surface. The preferred geometry of the cell culture chamber 270 is that of a flat, thin, space whose inner sides are all rounded and devoid of corners or vertices. An oval or rounded rectangular profile of the chamber is preferred. The flat surface and low height help to enable consistent fluid flows in the laminar flow regime, which in conjunction with low volumetric flow rates ensure low levels of fluid shear stress (order of 0.1 dyn/cm$^2$). Higher levels of shear stress would be disruptive to cells within the chamber and can reduce both cell viability and yield. Therefore, an important feature of the cassette is that it minimizes exposure of the cells within to high shear stress. This is accomplished by the use of a flat surface with a minimum of protuberances or surface roughness, by the avoidance of sharp boundaries within the fluid pathway and within the cell culture chamber 270, by the use of laminar flow where possible (which is enhanced by keeping the cell culture chamber 270 thin, such as from about 0.1 mm to about 2 mm in height), and by the inclusion of a bubble trap or gas venting mechanism for the elimination of gas bubbles during perfusion of the cell culture chamber 270. Both the achievement of laminar flow and the elimination of gas bubbles are promoted by the positioning of inlet and outlet ports at opposite sides of the cell growth chamber, such as shown in FIG. 6A. Further, the cassette can be mounted at an angle, with the outlet port positioned above the level of the inlet port, to assure that any bubbles entering the cell growth chamber through the inlet port are quickly eliminated at the outlet port by rising to the outlet port, aided by their buoyancy.

Figure 6B:
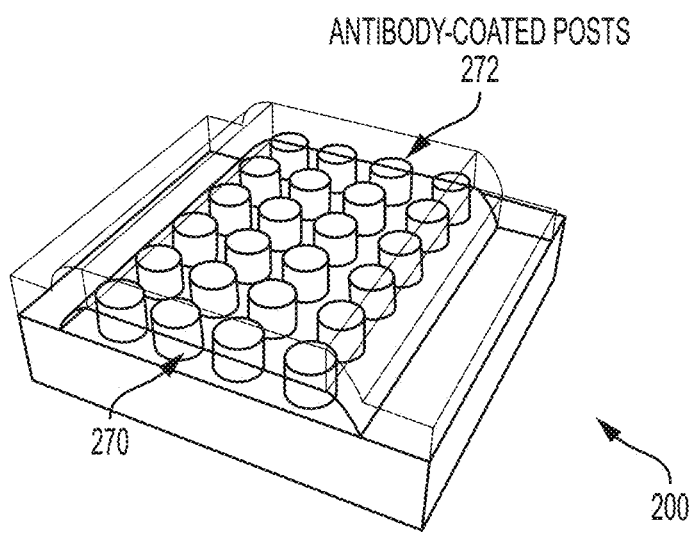
FIG. 6B shows a different embodiment of a dendritic cell differentiation cassette containing post structures within the cell culture chamber; the posts form part of a monocyte binding surface.

While the configuration shown in FIG. 6A is preferred, other configurations are also contemplated. For example, in order to increase media exposure to adherent cells, the middle layer of the device (cell culture chamber slab) can be made very thin, even omitting the cell culture chamber slab and using only one double-sided adhesive layer rather than the adhesive/PMMA/adhesive that is depicted in FIG. 6A. Posts 272, such as shown in FIG. 6B, or other structures such as a sinusoidal channel or an array of chambers, can be included in the cell culture chamber 270 in order to increase the surface area available for adhesion of cells, such as MCs. Vertical wells can be added to each side of the device by adding further layers to the device. Such vertical structures can be useful to trap cells that become non-adherent. A self-contained fluidic pump also can be included, especially in conjunction with one or more internal fluid reservoirs and valves, which can eliminate the need for an external pump and tubing as well as external culture medium reservoirs. Reservoirs for one or more cytokine stock solutions can also be included; if processor controlled valves are also included, this can avoid the need to switch the culture medium supply and thereby reduce or eliminate the chance of contamination.

A dendritic cell generating module of the invention includes at least a cell culture chamber, a pump, a culture medium reservoir, and fluidic connections between the medium reservoir, the pump, and the cell culture chamber. The module can also be provided without the cell culture chamber, which can be added to the module by the user, optionally together with one or more tubes for connecting the culture medium reservoir to the pump and DC differentiation cassette. The cell culture chamber can be provided as part of one or more dendritic cell differentiation cassettes as described above, or as one or more different structures.

In certain embodiments, the culture medium reservoir can be provided as one or more capped bottles either contained within the dendritic cell generating module or fluidically coupled to the module. Each reservoir contains an inlet port and an outlet port, or an outlet port and a vent fluidically coupled to the fluid inlet port of the one or more dendritic cell differentiation cassettes; a fluid collection reservoir fluidically coupled to the fluid outlet port of the one or more dendritic cell differentiation cassettes; and a pump configured for pumping fluid from the culture medium reservoir, through the cell culture chamber of the one or more dendritic cell differentiation cassettes, and into the fluid collection reservoir.

Figure 7A:
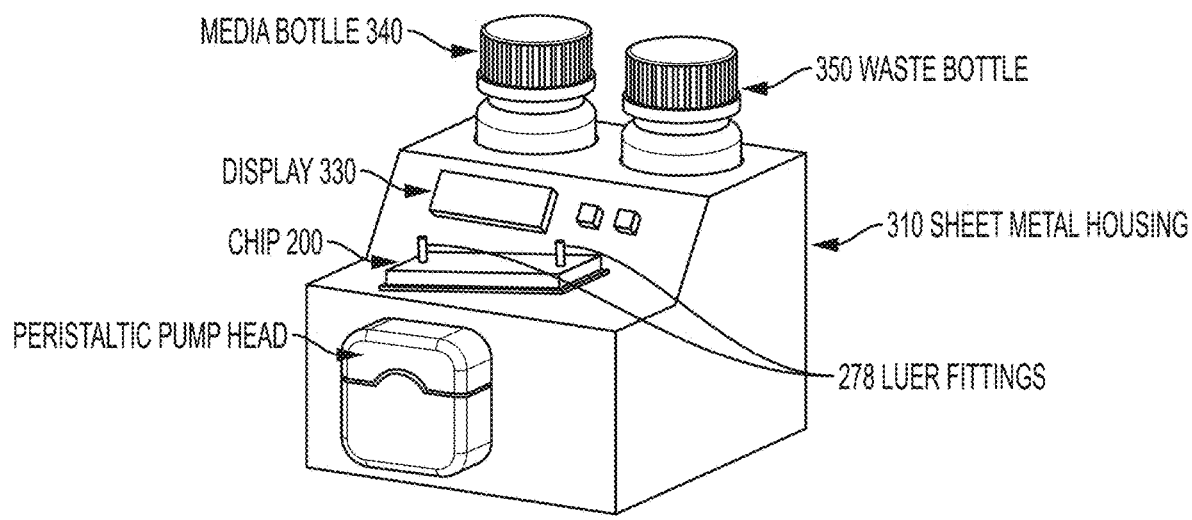
FIG. 7A shows an embodiment of a dendritic cell generation system according to the present invention.

An embodiment of a DC generating system is depicted in FIG. 7A. The system includes a housing with spaces for containing a culture medium reservoir and a waste reservoir (each the size and shape of commercially available glass or plastic culture medium bottles with plastic caps), a mounting area for a DC differentiation cassette, an exposed peristaltic pump head configured for accepting peristaltic pump tubing leading from the culture medium bottle to the inlet port of the cassette (another tube leading from the outlet port of the cassette to the waste bottle does not need to pass through the pump head), a display, and control buttons, knobs, or switches. This system can also include a heater for controlling the temperature of the cassette and optionally the culture medium reservoir; in such a configuration, no incubator is required, and the system can operate autonomously, with only a source of electrical power. If the system lacks a heater, it can be operated inside of a cell culture incubator. Similar systems that include two or more cassettes and pump heads (e.g., one for each cassette, such as 2, 3, 4, 5, 6, 7 8, 9 10 or more cassettes and pump heads) are also contemplated. In such multi-cassette systems, the control electronics, display, and buttons, knobs, or switches can either be shared among the different cassettes, or duplicated with one set for each cassette.

Figure 10A:
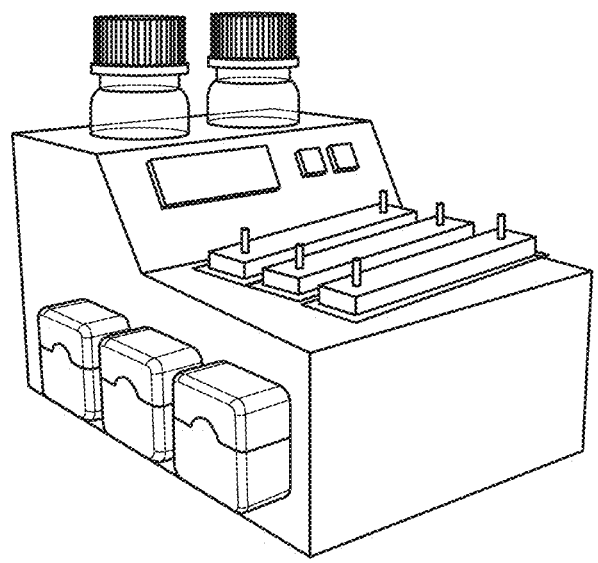
FIGS. 10A and 10B show a schematic illustration of a dendritic cell generation system according to the invention where the pumps are not mounted on the cell culture chamber chips.
Figure 10B:
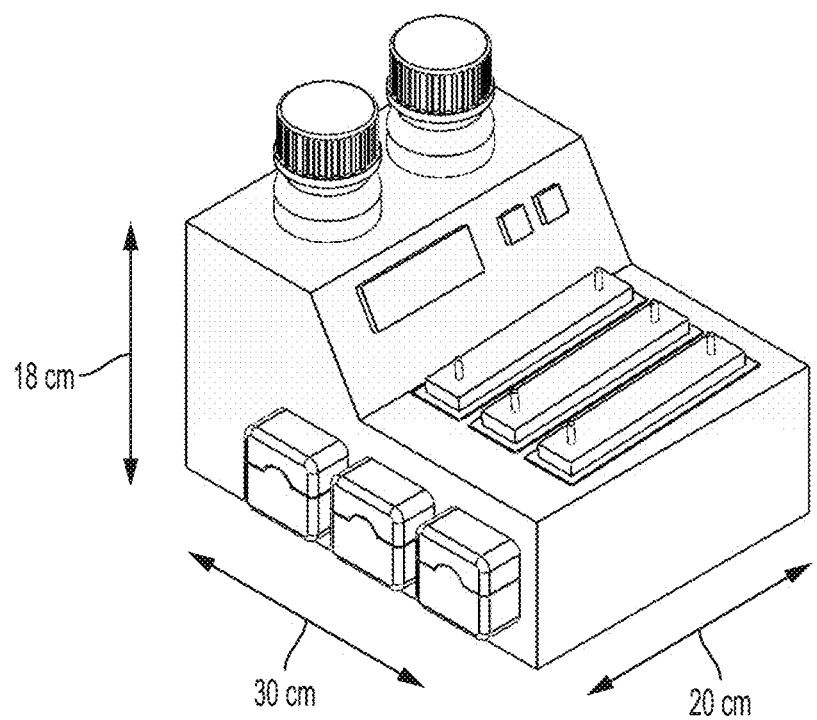

It is to be understood that the dendritic cell generating module can also be provided as a standalone dendritic cell generation system that does not include the cellular material processing module, the co-culturing module, and the concentrating module. For example, FIGS. 10A and 10B show a schematic illustration of a dendritic cell generation system that includes multiple dendritic cell generating modules. As shown, the dendritic cell generation system contains three modules, although it is to be understood that systems of the invention are not limited to three modules and can include any number of modules, such as one, two, three, four, five, six, seven, eight, nine, ten, fifteen, twenty, thirty, forty, fifty, sixty, seventy, eight, ninety, one hundred, or any number of modules in between or higher than one hundred.

Alternatively, the dendritic cell generating module can be provided in a system containing modules for effectuating various other processes prior to, concurrent with, or subsequent to the process occurring within the dendritic cell generating module.

Implementations of the dendritic cell generating module in accordance with the invention have certain advantages. For example, the fluidic systems described throughout the present disclosure provide at least one dendritic cell generation module that can culture cells using a filterless construction. By maintaining the fluid flow rate below the sedimentation rate, dendritic cells remain within the culture chamber because of their mass. In other words, dendritic cells will sink towards the bottom of the cell culture chamber and therefore remain in the cell culture chamber without requiring a filter. This simplifies the overall design of the system and improves, for example, the required maintenance of the system. A filterless system will not suffer clogged filters or require that a filter be replaced for example.

A flow rate that is lower than the sedimentation rate can be calculated according to Equation 1:

$$v\_max = [(\psi d\_p)]^2/150 \ \mu g(\rho\_cell - \rho\_liquid)\epsilon^3/(1-\epsilon) \quad \text{Equation 1}$$

where v_max is the liquid velocity beyond which cells will be lifted upwards, ψ is shape factor of cells (ratio of surface area of the cells to surface area of a sphere of equal volume; note that cells are not perfectly spherical and this factor is expected to be below 1), d_p is a diameter of a spherical particle of volume equal to that of a cell, μ is viscosity of liquid containing cells, g is the gravitational constant ρ_cell is the density of cells, ρ_liquid is a density of liquid containing cells, and ε is a fraction of the volume of interest that is not occupied by cells.

In some examples, the inlet and outlet of the cell culture chamber are set at an angle. That is, the inlet and outlet are disposed on opposite sides of the cell culture chamber and the outlet is positioned at a height above the inlet. This arrangement functions as a "bubble trap" as bubbles within the cell chamber are unable to form in the cell chamber. This bubble trap feature provides multiple advantages to the system. For example, by preventing bubbles, the bubble trap ensures uniform shear forces applied to the cells within the chamber. In addition, if bubbles were to form, these bubbles would block a cell's access to media/fluid, which in turn would cause those cells to die. By preventing bubble formation, the cell viability is enhanced. Finally, bubbles within the cell culture chamber would also cause irregular fluid flow, which is also prevented by the bubble trap.

In some embodiments, fluid for the dendritic cell generation module is perfused outside of the cell culture chamber. In some examples, the dendritic cell generation module not only simplifies the required culture steps, but also consumes an amount of medium roughly equivalent to the volumes consumed during manual culture. This feature eliminates additional costs due to wasted medium. In some examples, the medium consumption is less than 25 milliliters (e.g., less than 5, 10, 15, or 20 milliliters) of the culturing fluid.

Once the dendritic cells are generated, they are flowed from the dendritic cell generation module to an inlet of the co-culturing module via the fluid outlet of the dendritic cell generation module.

Cellular Material Processing Module

Systems of the invention include one or more cellular material processing modules. The cellular material processing module receives a sample of cellular material associated with a disease from the patient, for example a cellular material expressing a cell-surface antigen (e.g. a cancer antigen). The cellular material can be tumor material or can be non-tumor material, for example a non-tumor material that is transfected to express a cell-surface antigen.

Exemplary cellular material samples include but are not limited to: solid tissue as from a fresh, frozen and/or preserved organ, tissue sample, biopsy, or fine needle aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

In one embodiment, the sample is a tumor sample, e.g., a sample including one or more premalignant or malignant cells. In certain, embodiments, the sample is acquired from a solid tumor, a soft tissue tumor, metastatic lesion, surgical margin, malignant pleural effusion, malignant ascites, and bone marrow. In certain aspects, the sample is a digested solid tumor tissue. In other aspects, the sample is a fine needle aspirate.

By combining cellular material, such as tumor material, with dendritic cells from a patient, the resultant immunotherapeutic product can present a broad array of antigens targeted for the patient's specific tumor, which can be helpful in diverse tumors, such as multiple myeloma, due to the ability of the resultant product to stimulate a broader antitumor response.

In certain embodiments in which the sample is a tumor tissue material, the sample undergoes mechanical disruption, digestion, and or other processing steps within the module. In one aspect, the processing breaks the tumor tissue down into individual cells. In another aspect, the processing releases the internal contents of the cells. A variety of techniques for releasing the contents of the cells are known in the art and can be used with the fluidic systems and in the dendritic cell generation module in specific. See e.g., the techniques described by Maniatis, et al., Molecular Cloning: A Laboratory Manual, 1982, Cold Spring Harbor, N.Y., pp. 280-281; Sambrook and Russell, Molecular Cloning: A Laboratory Manual 3Ed, Cold Spring Harbor Laboratory Press, 2001, Cold Spring Harbor, N.Y.; or as described in U.S. Pub. 2002/0190663.

Once the tumor tissue sample has gone through one or more processing steps and a single cell suspension can be generated, the suspension can be flowed from the dendritic cell generation module to the co-culturing module.

In other embodiments, cells can be isolated from malignant ascites, pleural effusions, or other liquid sources of cellular material, such that the cellular material is already in a liquid suspension form. In one embodiment, the liquid based cellular material can be passed straight through to the co-culturing module, such that the cellular processing module acts as a flow-through channel. In another embodiment, residual red blood cells (RBCs) can be lysed from the liquid based cells. In one aspect, lysis is performed in a single chamber with optional venting. In another aspect, lysis is performed as a two-step lysis at different temperatures, each of the steps being performed in a separate chamber.

In certain embodiments where the cellular material is not obtained from tumor material, the cellular material can be transfected to express a cell-surface antigen. For example, the cellular material is transfected with a nucleic acid molecule that encodes a polypeptide comprising the antigen. Exemplary cell-surface antigens are MUC1, α-fetaprotein, γ-fetaprotein, carcinoembryonic antigen, fetal sulfoglycoprotein antigen, $α_2$H-ferroprotein, placental alkaline phosphatase, and leukemia-associated membrane antigen. Methods for transfecting antigens are well known in the art.

Similar to the dendritic cell generation module, each of the above described processes that occur with the cellular material processing module are automated and occur in, for example, one or more chambers connected by one or more channels.

Once a cellular suspension is obtained, the suspension is flowed from the cellular material processing module to an inlet of the co-culturing module via the fluid outlet of the cellular material processing module.

Co-Culture Module

The cellular material from the cellular material processing module and the dendritic cells from the dendritic cell generation module can be combined in the co-culture module to produce a cell-based immunotherapeutic product. The co-culturing module is in fluidic communication with both the dendritic cell generation module and the cellular material processing module, such that the outlets of the dendritic cell generation module and the cellular material processing module are in fluidic communication with one or more inlets of the co-culture module to effectuate the flow of processed cellular material and dendritic cells into the co-culture module.

The cellular material and dendritic cells can be provided to the co-culture module in a ratio (cellular material:dendritic cells) from about 100:1 to 1:1000 of about, such as, for example and not limitation, 100:1, 75:1, 50:1, 25:1, 20:1, 15:1, 10:1, 5:1, 4:1, 3:1, 2:1, 1:1, 1:2, 1:3, 1:4, 1:5, 1:6, 1:7, 1:8, 1:9, 1:10, 1:15, 1:20, 1:50, 1:75; 1:100, 1:200:1:300, 1:400, 1:500, 1:600, 1:700, 1:800, 1:900, 1:1000, or any ratio therebetween. In one aspect, a ratio lower than 1:1 is preferred where the non-dendritic cells proliferate heavily in culture.

Within the co-culture module, the processed cellular material is contacted with the generated DCs under a condition that allows for the combination of the material to produce a cell-based immunotherapeutic product (e.g. a fusion product). Agents for aiding in the combination, or fusion, of these cells include but are not limited to polyethylene glycol, electricity or Sendai virus. See e.g., U.S. Patent Application Publication No. 2002/0041868 to Nicolette et al, which is herein incorporated by reference in its entirety.

The cells are cultured for a period of time in a culture medium to allow for their combination, or fusion. In one aspect, the culturing occurs in a cell culture chamber, similar to the one provided in the dendritic cell generation module. Exemplary culture mediums include, but are not limited to one or more of hypoxanthine, aminoptern, and thymidine. In one embodiment, the medium is a combination of all three (e.g., "HAT"). Any other suitable culture medium known in the art can be used in accordance with the present invention.

The cells can be cultured for a period of anywhere from less than a minute to several days. The duration of culture is dependent on the extent of stimulation desired. Generally, exposure of the dendritic cells to the tumor material for a period of under 24 hours is sufficient. However, if there is insufficient tumor material or more than one type of material (e.g. whole tumor cells and non-cellular material), longer periods of culture, over a period of multiple days, may be needed. In one embodiment, mixing can be provided to the cellular mixture to assist with the formation of the cell-based immunotherapeutic product.

After the cells have been cultured for a desired period of time and a plurality of cell-based immunotherapeutic products have been produced, the products can be flowed from the co-culturing module to a concentrating module. Alternatively, the steps described below with respect to the concentrating module also occur within the co-culturing module, such that only one module is provided for culturing and concentrating the cell-based immunotherapeutic products.

Concentrating Module

As described above, the concentrating module is provided to concentrate and wash the cell-based immunotherapeutic product generated in the co-culturing module. The concentrating module is in fluidic communication with the co-culturing module, with an inlet of the concentrating module fluidically coupled to an outlet of the co-culturing module.

The concentration of cell-based immunotherapeutic products can include any number of methods for concentrating cell-based products (e.g., eliminating cells that did not combine to form a cell-based immunotherapeutic product). Exemplary separation, or concentration, methods include traditional methodologies such as adherence techniques (which rely on the adherence properties between the cells of interest and other cells), density based techniques, such as centrifugation or resetting, filtration techniques, and antibody-binding techniques (e.g., fluorescence-activated cell sorting (FACS) and magnetic-activated cell sorting (MACS). Exemplary concentration methods also include microfluidic techniques, such as the use of micro-scale filters or pillars to separate cells based on size and membrane deformability, field flow fractionation (FFF; combines parabolic flow within a microfluidic channel and an external field), acoustophoresis (based on membrane deformation or elasticity and occurs when a high-pressure sound wave interacts with a cell), and dielectrophoresis (based on the differential polarization of particles within a non-uniform electric field). See, for example, Tomlinson et al., J Tissue Eng Dec. 28, 2012, incorporated by reference, which provides an overview of various concentration methods known in the art.

In one embodiment, given that the combined products having a higher density than those cells that did not combine, a method for concentrating the products includes centrifugation.

In another aspect, concentration of the cell-based products includes incubation in a HAT reagent. The reason for the effectiveness of the HAT reagent is that a number of tumor cell lines are sensitive to HAT due to lack of functional hypoxanthine-guanine phosphoribosyl transferase ("HGPRT"). The cell-based immunotherapeutic products formed by DCs and these tumor cell lines become resistant to HAT, as the DCs contribute functional HGPRT. Thus, a HAT selection can be performed after the DCs and processes cellular material have been combined to eliminate unfused parental cells.

In another aspect, concentration of the cell-based products includes separation via adherence to a substrate, such as the surface of an incubation chamber. The success of this method is dependent upon the different adherence properties between the cell-based product and cells that did not combine. For example, if the cells that did not combine are more adherent than the combined product, e.g., in the case of carcinoma cells, the cell mixtures can be cultured in an appropriate medium for a short period of time. Subsequently, the combined product can be gently dislodged and aspirated off, while the cells that did not combine grow firmly attached to the wall of the incubation chamber. Conversely, if the cells that did not combine grow in suspension, after the culture period, they can be gently aspirated off while leaving the combined product loosely attached to the surface of the incubation chamber.

In yet another aspect of the invention, the cell-based material can be subjected to filtration, such that one or more filters provided to the concentration module filter out material other than the cell-based immunotherapeutic product.

Depending on the separation method(s) used when carrying out the methods of the invention, in certain aspects of the invention, the concentration of the cellular-based products can be carried out within one or more centrifugation chambers, one or more incubation chambers (e.g., HAT incubation and adherence techniques) and/or one or more a flow-through chambers (anti-body based techniques) within the concentration module. In accordance with the present invention, the one or more chambers are in fluidic communication with the fluid inlet and the fluid outlet of the module, such that fluid enters the module from the fluid inlet, into and through the one or more incubation chambers, and to the fluid outlet.

Additionally, one or more wash steps can be performed within the concentration module wherein a wash solution is provided to the cells. The wash solutions can be contained in one or more reservoirs of the system, with the wash solution being introduced to the concentration module through a separate inlet in the module. In one aspect, the module also includes a separate outlet, and optionally an associated waste container, fluidically coupled to the concentration module through which used wash solution and unwanted cells flow.

In one aspect, the cell-based products are washed with a serum-free medium (SFM), for example polyethylene glycol and phosphate buffer saline (PBS). It is to be understood that the cell-based products can be concentrated and subsequently subjected to one or more consecutive wash steps. Additionally, the cells can be subjected to two or more cycles of concentration and subsequent wash step(s).

Once the cell-based products have been concentrated and washed, the products can be flowed from the concentration module (or the combined co-culturing/concentration module) via the fluid outlet of the concentration module and directly to collection. From there, the cell-based immunotherapeutic products can be immediately delivered to a patient and/or the products can be placed in storage.

Fluidic Systems

As described above, systems and methods of the invention utilize modules that are fluidically coupled to one another for carrying out various aspects of processing a patient's blood and tumor samples to produce an immunotherapeutic product.

Fluidic systems, or devices, of the invention are modular and capable of fluidic connection to other similar devices in series (i.e., with fluid flowing from one device into another) and/or in parallel, and may also be so configured as to physically stack with one another or be capable of physical arrangement within a related device such as an incubator. The modular design of the system specifically allows for modules to be flexibly switched in and out depending on desired process to be included within the system.

Fluidic devices of the invention, including the cellular material processing, dendritic cell generating, co-culturing, and concentrating modules, can be provided in either a microfluidic embodiment (i.e., wherein one or more channels or chambers therein has a dimension in the range of from about 1 μm to about 999 μm) or a macrofluidic embodiment (wherein all of the channels or chambers therein have dimensions of about 1 mm or more), or both. The fluidic devices can further include fluid reservoirs, additional fluid channels or compartments, gaskets or seals, mixing zones, valves, pumps, vents, channels for pressurized gas, electrical conductors, reagents, ports, and tubing as required by a particular design. They also may contain one or more control modules, transmitters, receivers, processors, memory chips, batteries, displays, buttons, controls, motors, pneumatic actuators, antennas, electrical connectors, and the like. The devices preferably contain only materials that are nontoxic to mammalian cells and that are compatible with sterilization by the use of alcohol and/or heat or other means, such as exposure to gamma radiation or ethylene oxide gas.

The fluid reservoirs collectively act as buffer elements between the different steps to seamlessly connect the processes, which have various volumetric throughputs, such that continuous flow may be achieved throughout the device (although discontinuous flow/stop flow, may also be used within the systems and methods of the invention). The materials of equipment are chosen with the appropriate chemical compatibility under different temperature and pressure rating specific to each process. Additionally, the choice of pumps implemented in the device, such as syringe, peristaltic, pressure, and rotary pump, ranges from a nL to a mL in flow rates and 10 to 10,000 psi in pressure depending on the flow and pressure requirements for the different functions.

Systems of the invention can also include one or more sample solution reservoirs or well or other apparatus for introducing a sample to the device, at various inlets of the modules, which are in fluidic communication with an inlet channel. Reservoirs and wells used for loading one or more samples onto the fluidic device of the present invention include but are not limited to, syringes, cartridges, vials, eppendorf tubes and cell culture materials (e.g., 96 well plates).

Where needed, surfaces of the devices can be made more hydrophilic, such as by exposure to a plasma, or can be coated with one or more gels, chemical functionalization coatings, proteins, antibodies, proteoglycans, glycosaminoglycans, cytokines, or cells. The devices are also preferably compatible with use within a standard mammalian cell culture incubator, and in some embodiments do not allow the diffusion of gas through the material, as that could alter the composition of the culture medium within the device. Fluidic devices of the invention are preferably devoid of fluid leaks under operating conditions and capable of sterile operation over a period of days to weeks. Fluidic devices of the invention also include a sampling mechanism that allows fluid to be removed from the system for testing without introducing new material or contaminants to the system.

In certain aspects, at least part of the fluidic system comprises disposable components, some or all of which can be housed within a non-disposable frame. In other aspects, all components of the system are disposable. Furthermore, in some embodiments, the fluidic system includes a sample tracking component for tracking and documenting patient material.

At least one, and sometimes a plurality or all steps during the manufacturing process are monitored for product characteristics (e.g. purity and polymorphic forms) using a variety of inline process analytical tools (PAT) or miniaturized micro-total analysis system (micro-TAS).

The fluidic systems of the present invention are capable of controlling the direction and flow of fluids and entities within the system. The term "flow" means any movement of liquid or solid through a device or in a method of the invention, and encompasses without limitation any fluid stream, and any material moving with, within or against the stream, whether or not the material is carried by the stream. For example, the movement of dendritic cells, processed cellular material, and cell-based immunotherapeutic product through a system or in a method of the invention, e.g. through channels of a module of the invention, comprises a flow.

Systems of the invention can use pressure drive flow control, e.g., utilizing valves and pumps, to manipulate the flow of cells, reagents, etc. in one or more directions and/or into one or more channels of a fluidic device. However, other methods may also be used, alone or in combination with pumps and valves, such as electro-osmotic flow control, electrophoresis and dielectrophoresis (Fulwyer, Science 156, 910 (1974); Li and Harrison, Analytical Chemistry 69, 1564 (1997); Fiedler, et al. Analytical Chemistry 70, 1909-1915 (1998); U.S. Pat. No.

Systems of the invention can also include or be operably coupled to one or more control systems for controlling the movement of fluid through the system; monitoring and controlling various parameters, such as temperature, within the systems; as well as detecting the presence of cell-based immunotherapeutic products, quantity of product (directly or indirectly), conversion rate, etc.

Computer Implementation

Aspects of the present disclosure described herein, such as control of the movement of fluid through the system and the monitoring and controlling of various parameters, can be performed using any type of computing device, such as a computer or programmable logic controller (PLC), that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the present disclosure can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

In an exemplary embodiment shown in FIG. 17, system 600 can include a computer 649 (e.g., laptop, desktop, or tablet). The computer 649 may be configured to communicate across a network 609. Computer 649 includes one or more processor 659 and memory 663 as well as an input/output mechanism 654. Where methods of the invention employ a client/server architecture, an steps of methods of the invention may be performed using server 613, which includes one or more of processor 621 and memory 629, capable of obtaining data, instructions, etc., or providing results via interface module 625 or providing results as a file 617. Server 613 may be engaged over network 609 through computer 649 or terminal 667, or server 613 may be directly connected to terminal 667, including one or more processor 675 and memory 679, as well as input/output mechanism 671.

System 600 or machines according to the invention may further include, for any of I/O 649, 637, or 671 a video display unit (e.g., a liquid crystal display (LCD) or a cathode ray tube (CRT)). Computer systems or machines according to the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 663, 679, or 629 according to the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

EXAMPLES

Example 1. Fabrication of Dendritic Cell Differentiation Cassette

The dendritic cell differentiation cassette shown in FIG. 6A was fabricated for use with a variety of embodiments of the dendritic cell generation system of the invention, such as the embodiment shown in FIG. 7A. In this embodiment of the system, growth medium bottles having threaded access ports are utilized for the reservoir and waste containers to reduce the possibility of contamination during use. The monocyte binding surface area of the cassette's cell culture chamber was 17.41 cm$^2$, which was suitable for binding and differentiating monocytes contained in 25 mL of human blood. Silicone gaskets were cut to fit around the Luer connectors that are attached to the device; the gaskets prevent leaking through the tapped holes. The monocyte binding surface area of the cassette's cell culture chamber was 17.41 cm$^2$, which was suitable for binding and differentiating monocytes contained in 25 mL of human blood.

FIG. 6A shows a schematic representation of the components used to construct the cassette. The components are, from top to bottom: PMMA lid 250 with threaded holes 260 for addition of Luer fittings (shown as 278 in FIG. 7A), double-sided adhesive 240 (with liners still on), PMMA channel 230, double-sided adhesive 220 (with liners still on), and polystyrene bottom 210. The fluidic device was designed to carry out perfusion based cell culture, and was constructed using three layers of thermoplastic material joined by adhesive transfer tape. The part designs were created using CAD software and then transferred to a laser cutter which allowed the plastic and adhesive to be cut to the specified size and shape, The thermoplastic bottom layer was made of clear 0.05" thick polystyrene that was cut into a rectangle shape slightly larger than the other layers to account for the melting and deformation that laser cutting causes in polystyrene. The polystyrene was then oxygen plasma treated to make the monocyte binding surface more hydrophilic (similar to the treatment of standard polystyrene cell culture flasks). The second thermoplastic layer (cell culture chamber layer) was PMMA that was 1/16" thick. It was initially cleaned using a sonic toothbrush and Contrad 70 followed by rinsing with 70% ethanol. Then, one liner was removed from a section of acrylic adhesive tape (e.g., 3M 468MP Adhesive Transfer Tape), which was the same size as the PMMA. The adhesive layer was then carefully applied to the PMMA. Bubbles were removed, and the pressure-sensitive adhesive was activated by applying force with a laminating roller. This process was repeated on the other side of the PMMA, such that the PMMA had a layer of adhesive (and liner) on each side of it. This adhesive coated plastic was then laser cut to create a fluidic channel (cell culture chamber). The thermoplastic top layer served as a cover to the fluidic channel and was made from 3/16 inch thick PMMA. In addition, the top layer served as the base for inlet and outlet fluidic connections. The connections were made by laser cutting through holes which were then tapped manually to provide 10-32 threads for accepting 10/32 male Luer fittings. Fluid was later introduced to the system by connecting the Luer adapter to a blunt dispensing needle with tubing pushed onto the blunt needle portion. The top PMMA and bottom polystyrene layers were cleaned the same way as described above for the PMMA middle layer. The three layers were then combined by removing the remaining liner layers on the adhesive layers above and below the middle cell culture chamber slab one at a time and applying to the top and bottom layers. As before, pressure was applied using a laminating roller to active the adhesive. All steps described above were performed in a biological safety cabinet where possible to reduce the possibility of biological contamination.

Example 2. Dendritic Cell Generation System

Figure 7B:
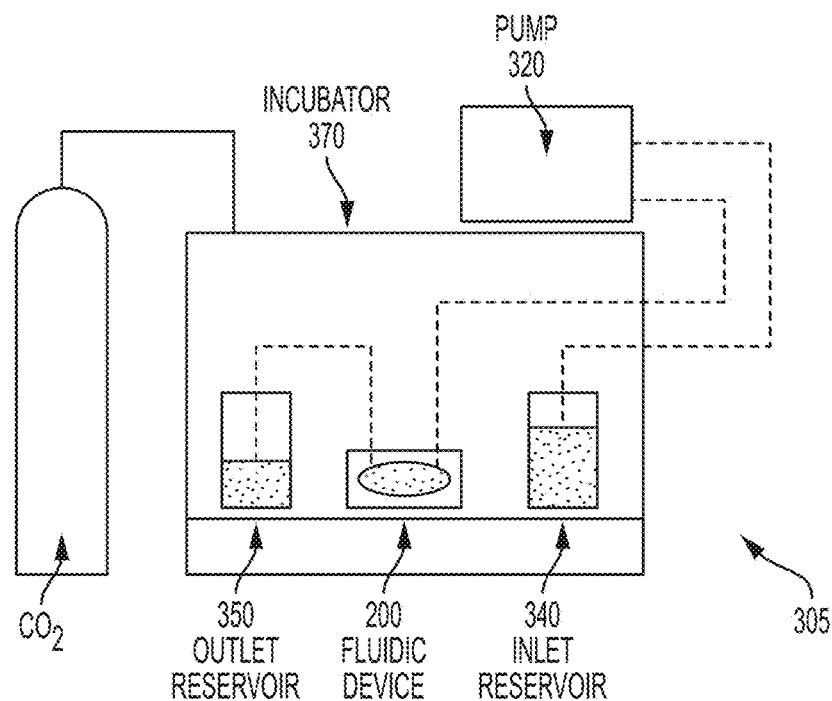
FIG. 7B shows a schematic illustration of another embodiment of a dendritic cell generation system according to the invention.
Figure 7C:
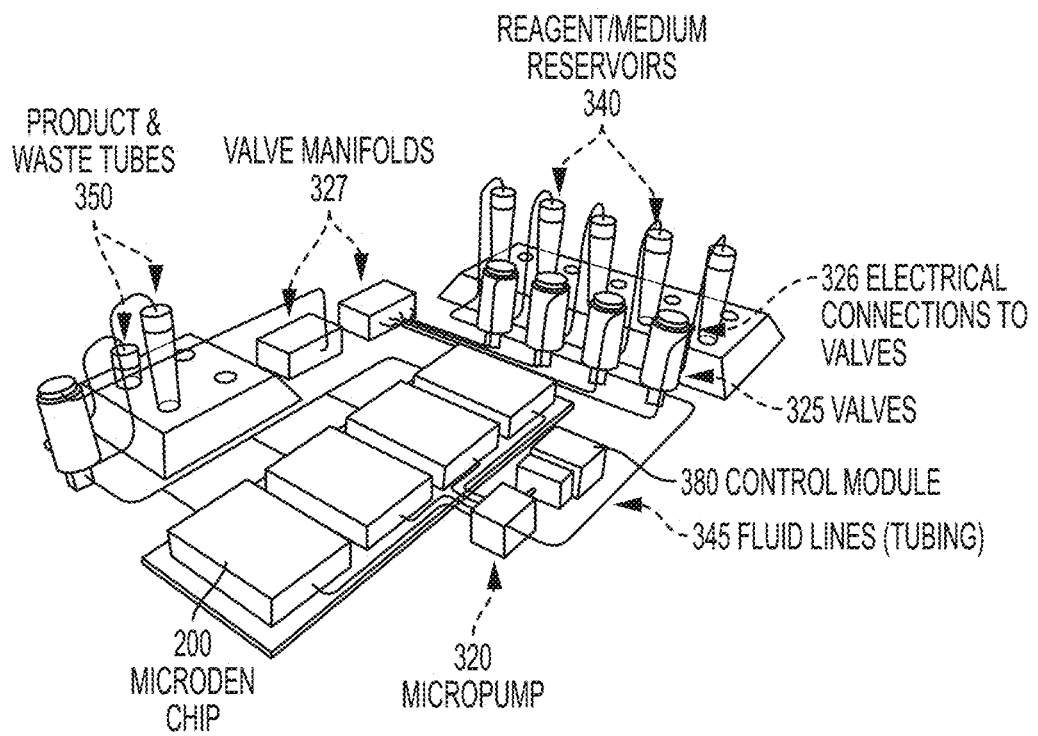
FIG. 7C shows a schematic illustration of yet another embodiment of a dendritic cell generation system.

A dendritic cell generating system as shown in FIG. 7B was set up. The system included the dendritic cell differentiation cassette described in Example 1 plus several other components. An ordinary mammalian cell culture incubator (maintained at 37° C., 5% CO$_2$, 95% humidity) was used to keep certain system components and the cells in the appropriate environment. Growth medium supply reservoir 340 and an effluent collection reservoir 350 were kept in the incubator. These reservoirs consisted of 100 mL culture medium storage bottles. Four port (1/4-28 threaded) caps were attached to the bottles to allow fluid removal and gas exchange. On one port, a sterile syringe filter was attached using appropriate connectors. The filter allowed gas exchange to occur without risking contamination of the growth medium. On two other ports, tubing was inserted to allow the media to be pumped to the remaining system. The fourth port was plugged. In order to pump the media to the rest of the system, the culture medium reservoir was connected to a peristaltic pump located outside of the incubator, with supply tubing passed through an access port of the incubator. The medium was then pumped into the incubator to the dendritic cell differentiation cassette and out the incubator to the fluid collection reservoir, which was set up similar to the supply reservoir. Small diameter tubing was used to reduce heat exchange while the medium was transiting through the pump outside the incubator.

Example 3. Whole Blood Sample Preparation

Approximately 25 mL of whole blood was obtained from a human subject in 4 sodium heparin coated vacutainers with the assistance of a phlebotomist. A cell separation was then performed in a sterile manner using Ficoll-Paque PLUS according to the following protocol. The whole blood was first diluted two times with PBS containing 10% ACD-A (acid citrate dextrose). The blood solution was then carefully layered on top of 15 mL Ficoll solution in each of two 50 mL conical centrifuge tubes. The tubes were centrifuged at 500×g at 4° C. for 30 minutes, with the brake on the centrifuge turned off to prevent disturbing the cell pellet. Following centrifugation, the blood components had separated into three distinct regions. The buffy coat, consisting of peripheral blood mononuclear cells (PBMCs) was located just below the plasma layer at the top of the centrifuge tube. To remove the PBMCs, the plasma was removed and discarded until only ~1 cm of plasma remained. The PBMCs (with some plasma) from each tube were then transferred to new 50 mL tubes and diluted with cold (4° C.) PBS containing 1 mM EDTA to a total volume of 45 mL. The tubes were then centrifuged at 270×g for 10 min at 4° C. with the brake off. Following centrifugation, the supernatant was removed, and the cells were combined into one tube and resuspended in cold PBS with 1 mM EDTA to a total volume of 45 mL. The cells are then centrifuged one final time at 130×g for 10 minutes at 4° C. with the brake set to a low value. After removing the supernatant, the cells were resuspended in 3 mL of dendritic cell conversion media and counted. A small aliquot (~0.25 mL) was removed for analysis by a flow cytometer, while the remainder was diluted to the necessary concentration for cell seeding in a dendritic cell differentiation cassette. The cell concentration was approximately $2\times10^6$ cells/mL, but could also be diluted as low as $5\times10^5$ cells/mL if more volume was needed.

Example 4. Culturing of Monocytes

Before beginning cell culture experiments, all components that were not sterile as purchased were rinsed with 70% ethanol followed by sterile growth medium. The dendritic cell differentiation cassette was filled with culture medium and allowed to incubate for at least an hour in the incubator. During this time, the inlet and outlet connections on the device were closed. After removing the medium, about 3 mL of cell solution (see Example 3) were then added to the cassette, which was then incubated for an hour to allow monocytes to attach to the hydrophilic polystyrene surface. After an hour, the medium was poured out of the cassette, removing any non-adherent cells. The medium was replaced with fresh medium, and the device was connected to the rest of the system for perfusion. Fresh culture medium was perfused using a low flow rate of 2 µL/min until the end of the experiment.

Example 5. Cell Viability

The dendritic cell generation system of Example 2 was tested for their ability to keep cells alive using the LIVE/DEAD cell viability assay (Molecular Probes L3224). PBMCs were isolated using a Ficoll separation as in Example 3 and plated as described in Example 4. To plate the cells, a 0.8 mL suspension of cells ($2\times10^6$ cells/mL) in RPMI 1640 culture medium containing 10% FBS and 1% pen/strep mixture was injected into four dendritic cell differentiation cassettes and allowed to incubate at 37° C. After 1 hour to allow for monocyte adhesion, the cassettes were flushed with fresh medium at a flow rate of 400 µL/min, after which flow was set to 10 µL/min. Individual cassettes were removed from the system on days 1, 3, 5, and 7 for analysis using the LIVE/DEAD assay. To label for imaging, the growth medium was removed from the cassette, and a PBS solution containing 20 µL of a calcein-AM solution (50 µM in DMSO) and 20 µL of an ethidium bromide solution (2 mM in DMSO/water, 1:4) was injected. The staining solution was allowed to incubate for 15 min at room temperature, and then the cassette was rinsed with fresh PBS. Imaging was performed using a Nikon microscope with a 20× objective and an integration time of 0.5 s. Cell fluorescence was analyzed by thresholding particles at 20% of the maximum signal and counting using the particle count tool of the ImageJ image processing software.

Figure 8:
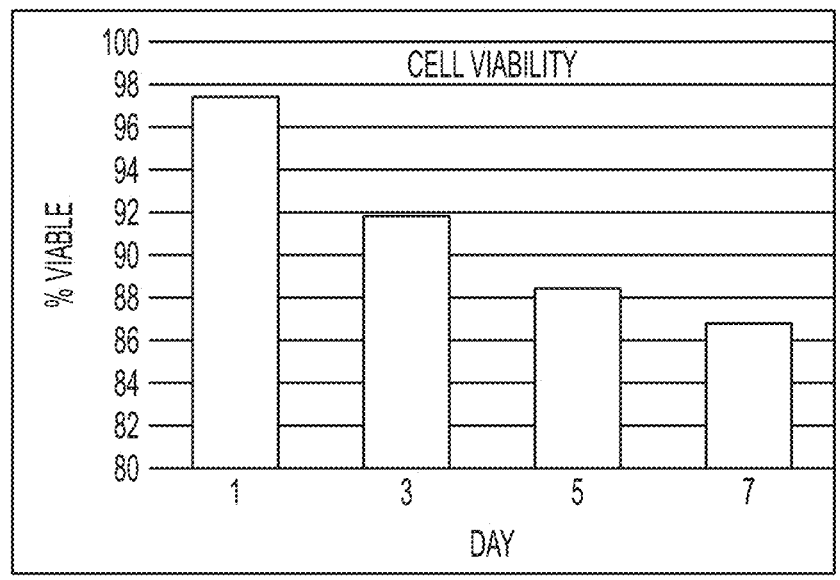
FIG. 8 shows a graph of the results of a cell viability assay carried out on cells perfused for up to seven days using a dendritic cell generation system of the invention.

Cell viability was maintained at over 86% throughout a 7-day period, as represented in FIG. 8 (note that the scale bar on the left starts at 80%). This indicated that most monocytes can survive long enough for a DC generation process that lasts up to seven days.

Example 6. Differentiation and Maturation of Dendritic Cells

To stimulate bound monocytes to differentiate into dendritic cells, the bound monocytes were subjected to continual perfusion over five days with conversion medium containing IL4 and GM-CSF. The conversion medium was prepared by mixing RPMI-1640 with IL4 to give a final concentration of 500 U/mL and GM-CSF to give 800 U/mL, and a final volume of 20 mL. The differentiation process resulted in detachment of dendritic cells from the polystyrene surface and their retention in the culture chamber, due to the slow flow rate, which was maintained at 2 µL/min. The differentiated, detached dendritic cells were matured by incubation in maturation medium containing IL1β (2 ng/mL), IL6 (1000 U/mL), TNFα (10 ng/mL), and PGE2 (111 g/mL) for an additional one day. Switching from one medium to another was performed by manually switching the inlet tubing from one medium reservoir bottle to another. Matured cells were recovered after the six-day culture protocol and were characterized by flow cytometry. Matured dendritic cells had a characteristic large and granular phenotype, and had the surface marker profile Lin1 negative, HLA-DR positive, and CD80 positive.

For flow cytometry, cells were first suspended in cold (4° C.) staining buffer (BD 554657) at a concentration between $1\times10^7$ and $2\times10^7$ cells/mL. A 50 µL aliquot of the cell suspension ($5\times10^5$ to $1\times10^6$ cells) was placed into a 1.5 mL centrifuge tube. The desired antibody-dye solution was added to the cell suspension at the manufacturer's recommended concentration. For these experiments, HLA-DR antibody conjugated with phycoerythrin (R&D Systems FAB4869P) and a lineage cocktail (Lin-1) consisting of different antibodies (antibodies against CD3, CD14, CD16, CD19, CD20, and CD56) conjugated to fluorescein (BD 340546) were utilized. This cocktail was formulated to mark several types of white blood cells but not dendritic cells. HLA-DR is a marker of immature dendritic cells and other white blood cells such as macrophages and B-cells, while the lineage cocktail contains markers for different types of white blood cells including CD14+ monocytes but not dendritic cells. These labels served as an indicator that monocytes had been converted into immature dendritic cells. Markers for mature DCS can include CD83 and CD86 labels. After adding the antibody conjugates to the cell solution, the solutions are mixed by gentle pipette titration and placed in a dark refrigerator at 4° C. for 1 hr. After the incubation, 1 mL of cold staining buffer was added to the centrifuge tube, and the cells were centrifuged at 300×g for 5 min at 4° C. to pellet the cells. After removing the supernatant, the labeled cells were resuspended in 0.25 mL of fresh staining buffer and stored in the dark at 4° C. until analyzed. If the analysis was to be done more than 24 hrs later, the cells were fixed with 4% paraformaldehyde 4° C.

Figure 9A:
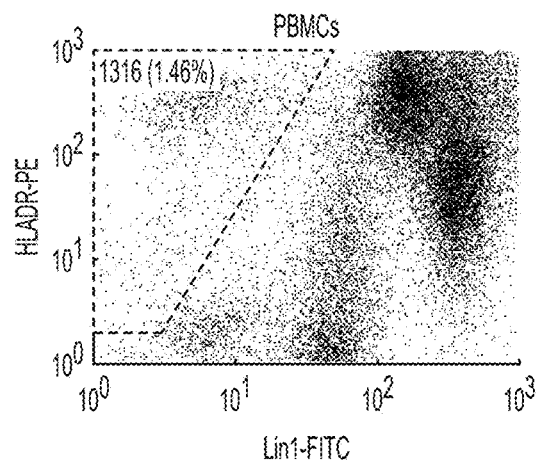
FIGS. 9A-9D show the results of an experiment to characterize the phenotype of PBMCs before use of the dendritic cell generators (FIGS. 9A and 9C), and DCs obtained after differentiation and maturation in the dendritic cell generators (FIGS. 9B and 9D).
Figure 9B:
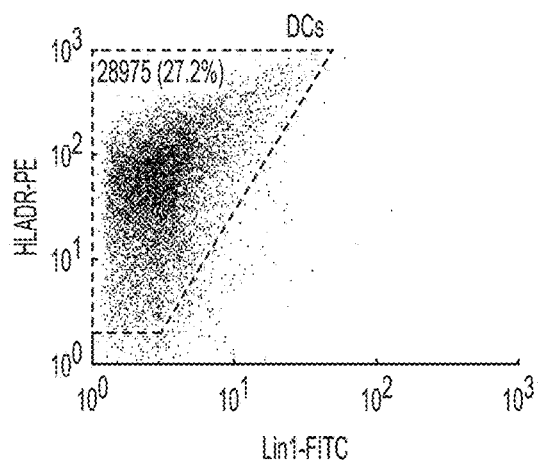
Figure 9C:
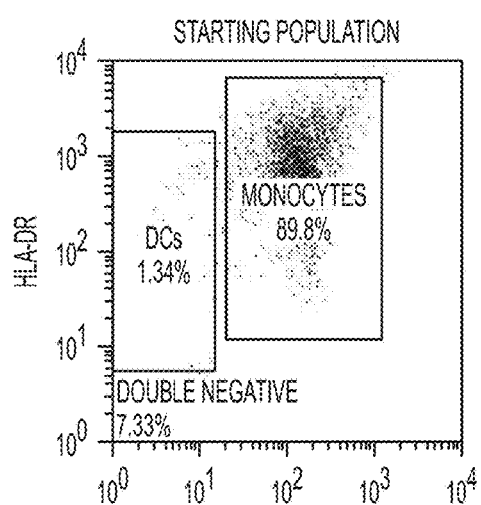
Figure 9D:
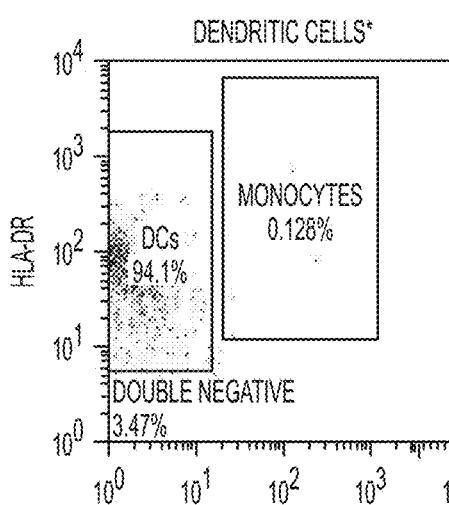

Before carrying out flow cytometry, background fluorescence levels and desired electronic volume range were set using an unlabeled sample. Flow cytometry results are shown in FIGS. 9A-9D. FIG. 9A shows results obtained for PBMC used for initial seeding of the dendritic cell generator system. FIG. 9B shows results obtained for the generated dendritic cells. In the PBMCs, several different populations of cells can be seen, which is indicative of the expected mixture of several different types of cells that were stained by both Lin-1 and HLA-DR antibodies. A sparse population of cells can be seen in the left side of FIG. 9A, which is where DCs are expected due to low Lin-1 expression and high HLA-DR expression. Only 1.46% of cells analyzed were found in this region. After DC generation, this region became much more heavily populated, with 27.2% of cells showing characteristics of DC. Additionally, FIG. 9C shows the population at initial seeding of the dendritic cell generator system, while FIG. 9D shows results obtained for the generated dendritic cells. As can be seen, of the cells analyzed, the starting population only comprises 1.34% DC and 89.9% MC, whereas, after DC generation, with 94.1% of cells showing characteristics of DC and only 0.128% of MC.

Example 7. Prototype of Microfluidic Dendritic Cell Generator

Figure 11D:
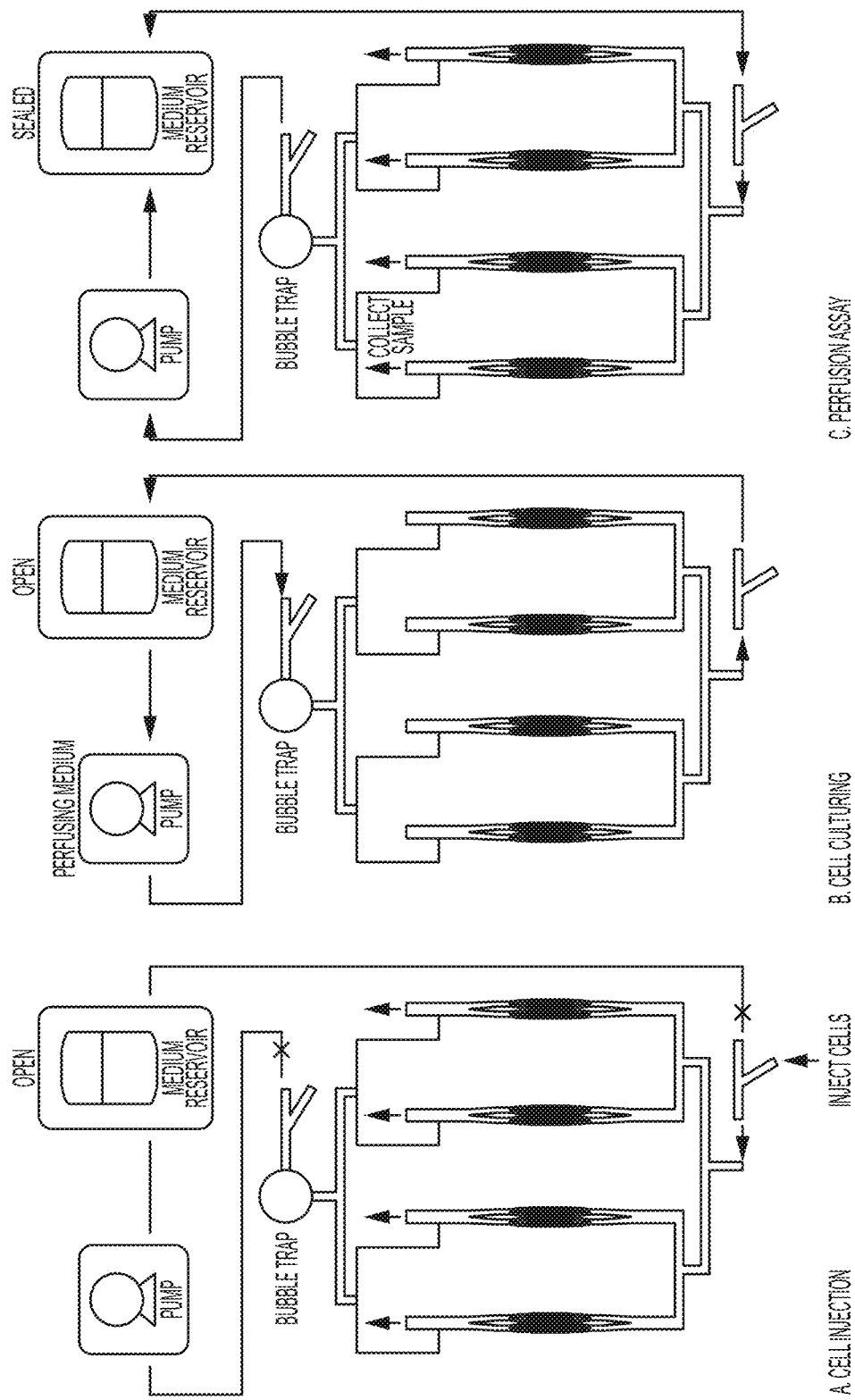

A standalone fluidic cell culture and perfusion platform for recapitulation of microvasculature is shown in FIG. 11A. As shown in FIG. 11B, four branching channel networks, connected in parallel, are coupled to a custom-designed, on-chip peristaltic pump. The pumping mechanism, comprised of a small motor and a rotating elliptical shaft, is capable of providing continuous and consistent flow of culture medium to the channel network. The flow rate can be controlled by adjusting the rotational speed of the metal shaft via changes in applied voltage (0-6 V corresponding to approximately 0-16 µL/min) as shown in FIG. 11C. FIG. 11C also shows that each of the four channels has the same flow rates in both forward and reverse direction, and the pump has little loss of stability over the 4-day time scale studied, a time scale similar to that required for the cell culture system. A bubble trap (FIG. 11B, D) was incorporated into this system to eliminate disruption of the cell culturing and subsequent mechanical detachment of the cell monolayers by air bubbles. Additionally, the pumping platform allows for direct injection of cells with the pumping mechanism turned off, which enables injection and loading of cells either via manual injection or at higher flow rates using an external pump.

Figure 12A:
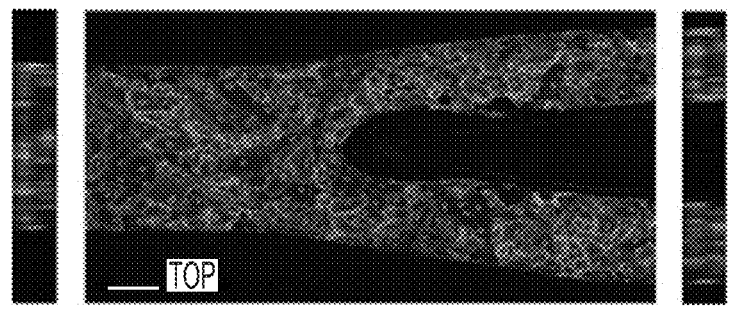
FIGS. 12A-12C show HUVEC cells cultured on chip that are viable and functional within 2 days. Immuno-fluorescence staining of the micro-vessel network shown as top view (middle) and cross sectional view of the circular channels (sides) in the micro-vessel network at (A) 400 µm segment, (ii) 200 µm segment, (iii) 100 µm segment. Scale bar, 100 µm; CD31-green, DAPI-blue. White arrows indicate void space between cells. Red arrows indicate the cross section of the 100 µm micro-vessels.
Figure 12B:
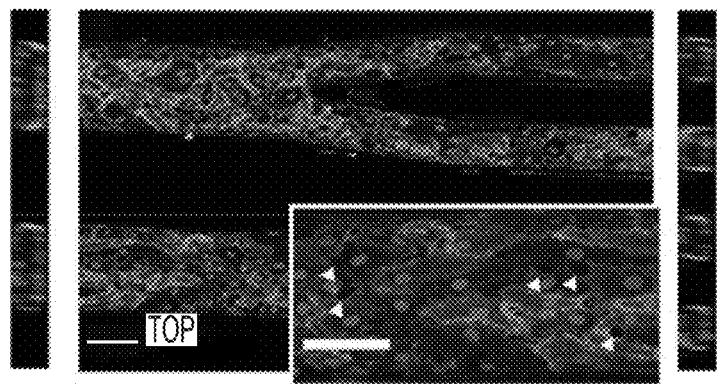
Figure 12C:
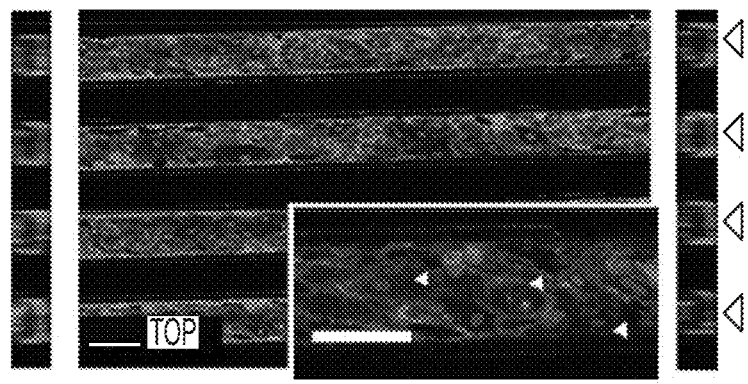
Figure 14D:
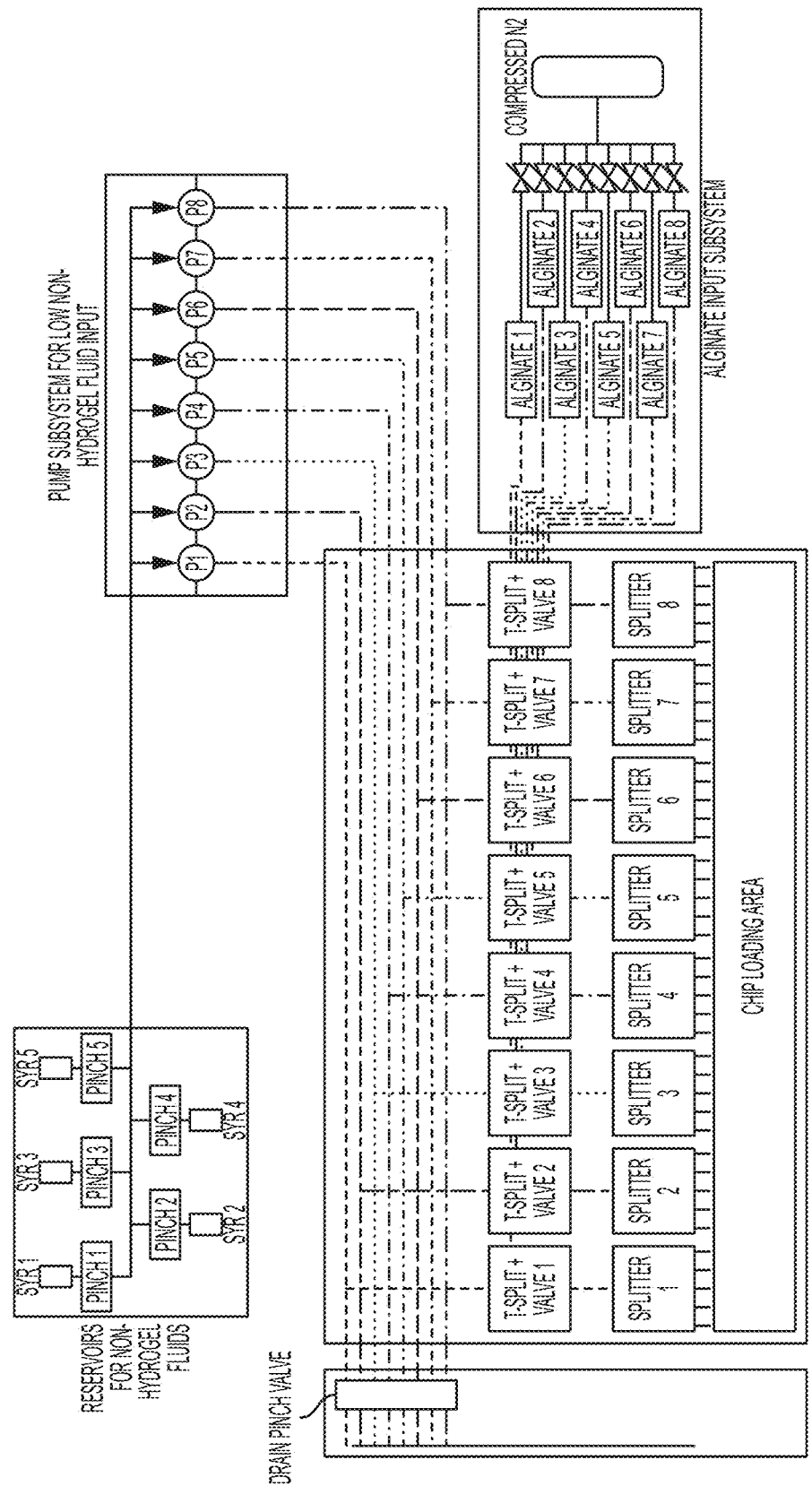
Figure 14E:
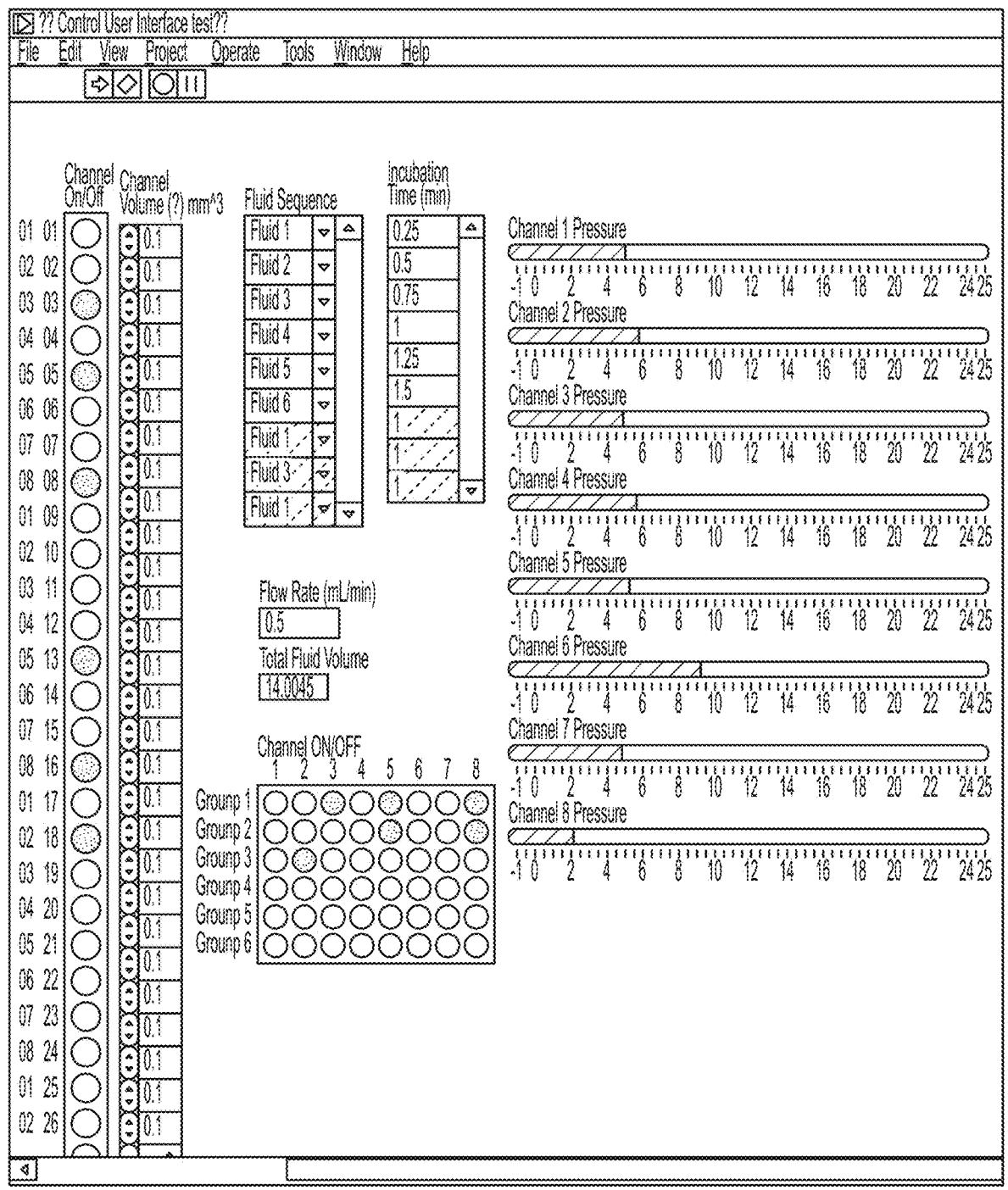

Within this device, HUVECs were able to attach, proliferate, and cover the entire luminal surface with pre-defined branching vessel structures within 2 days (FIGS. 12A-12C). This result also confirms that viability was not comprised by the micropump or any other aspect of the chip-based culture system. Expression of CD31 and VE-cadherin at the cell-cell interface outlined the endothelial morphology, confirming the formation of inter-cellular junctions. Cells aligned along the micro-channels in consistent with the morphology of endothelial cells in vivo which elongate and align in the direction of blood flow. The perfusion culture on chip resulted in a higher nitric oxide release upon introduction of acetylcholine, atorvastatin, and sildenafil compared to a well-plate static culture, demonstrating the benefit of recapitulating physiological conditions in terms of 3-dimensional geometry and fluid flow characteristics.

This system occupies a footprint of approximately 10 cm×5 cm and can be easily placed in a standard incubator for cell culturing at physiological conditions. The system can also be placed under a microscope for imaging while providing constant flow through the channels. While an external power source is needed, such sources are relatively small and a single source can be utilized to power multiple chips. In this work, the reservoirs all contained the same culture medium, but this system can be easily configured to add reservoirs for multiple types of media.

The coating is designed to combine antibody-mediated immunospecific capture with the non-specific adhesion affinity-based methods for microfluidic purification of multiple cell types from blood for over a decade. A significant contribution to this area was the design of surface coatings made of a copolymer of alginate and poly(ethylene glycol) (PEG) functionalized with capture antibodies as described in, for example, Hatch A, Hansmann G, Murthy S K. Engineered Alginate Hydrogels for Effective Microfluidic Capture and Release of Endothelial Progenitor Cells from Whole Blood. Langmuir. 2011; 27: 4257-4264 and Hatch A, Pesko D M, Murthy S K. Tag-Free Microfluidic Separation of Cells against Multiple Markers. Anal. Chem. 2012; 84: 4618-4621. This coating was designed to combine antibody-mediated immunospecific capture with the non-specific adhesion properties of PEG and the degradable nature of alginate. Native alginate solutions are free flowing liquids which form hydrogels in the presence of divalent cations (like calcium). These hydrogels have a consistency similar to Jell-O but thin layers of these hydrogels can be fully dissolved by bringing in contact with a chelator such as ethylene diamine tetraacetic acid (EDTA). This 'on-demand' dissolution capability is retained in the coatings which can capture cells expressing target antigens within microfluidic devices as shown in FIG. 13. These devices have hexagonal arrays of 100 µm vertical pillar structures to increase surface area for cell capture, as illustrated in FIG. 11B. Following the capture phase, the isolated cells can be eluted out of the chip by flowing in a solution of EDTA. As described below, this coating will be incorporate into the culture chip shown above to add the capability to capture CD14+ monocytes from whole blood The design and fabrication of the system uses building blocks described above in four major steps: incorporation of pillar array structures within the linear microchannels of the culture system prototype shown in FIG. 11 to increase surface area for efficient capture of monocytes from blood; modifying the placement of fluid reservoirs to allow placement of four unique fluid source vials and one large waste vial; (ii) coating of microchannels with 'capture-release' coating functionalized with antibodies against CD14 and initial testing with commercially available purified CD14+ human peripheral blood monocytes; and (iv) testing with whole human blood to ensure that 'capture-release' coating can capture CD14+ monocytes with high purity; and testing of perfusion with culture medium.

A computational technique to identify pillar array parameters (pillar diameter, offset, and length) as described in prior publications (e.g., Zhu B, Smith J, Yarmush M L, Nahmias Y, Kirby B J, Murthy S K. Microfluidic enrichment of mouse epidermal stem cells and validation of stem cell proliferation in vitro. Tissue Eng Part C Methods. 2013; 19: 765-773 and Green J V, Radisic M, Murthy S K. Deterministic lateral displacement as a means to enrich large cells for tissue engineering. Anal. Chem. 2009; 81: 9178-9182). Briefly, a coupled computational fluid dynamics (CFD) particle advection code will be utilized to track a uniform distribution of cells through the microchannel. A range of offsets from 0 (straight array) to 75 µm (hexagonal array) will be examined. Given the size of monocytes ~10 µm in diameter and taking into account the size range of non-target cells in blood (2-10 µm, including disc-shaped erythrocytes), as described in, for example, Sethu P, Sin A, Toner M. Microfluidic diffusive filter for apheresis (leukapheresis). Lab Chip. 2006; 6: 83-89, an offset can be optimized to ensure that cells larger than 8 µm collide with at least 70% of the pillars. These arrays are created in rectangular cross-section PDMS microchannels via standard soft lithography. Microchannels with 400 µm widths with 10-20 µm diameter pillars are used as the starting point. While a branch channel is shown in FIG. 11, it is not required.

As shown in FIG. 11A, the media reservoir tubes are seated in a custom-designed PDMS block. A similar block will be created to house four 2 mL vials for reagents and a larger mL tube for waste. An additional slot will be created for a product vial. Note that this preparation is for device operation in a 'semi-manual' mode where source and exit tubes will be moved manually between reservoir tubes and waste/product tubes.

PEG-alginate hydrogel coatings will be prepared as described previously in, for example, Hatch A, Hansmann G, Murthy S K. Engineered Alginate Hydrogels for Effective Microfluidic Capture and Release of Endothelial Progenitor Cells from Whole Blood. Langmuir. 2011; 27: 4257-4264, applied onto the surfaces of the pillar-array microchannels with a surface coating of anti-CD14 capture antibody (Abcam). Performance testing of the pillar array includes the capture of commercially available purified CD14+ human peripheral blood monocytes (Lonza). Cells will be flowed into the channels at flow rates corresponding to wall shear levels of 0.3-0.5 dyn/cm$^2$, which is an optimal range for CD14+ cell capture identified by Cheng and coworkers (See, for example, Cheng X H, Gupta A, Chen C C, Tompkins R G, Rodriguez W, Toner M. Enhancing the performance of a point-of-care CD4+ T-cell counting microchip through monocyte depletion for HIV/AIDS diagnostics. Lab Chip. 2009; 9: 1357-1364). Following capture and a wash with PBS, cells are eluted out using a solution of 50 mM EDTA in PBS and counted using a Beckman Coulter Quanta SC benchtop flow cytometer. The design can be further optimized until the capture level of monocytes is maximized. For a typical transcriptomics experiment with CD4+ T cells, for example, ~3×10$^5$ DCs which are generated by a comparable number of monocytes. The size and total area of microchannels and pillar arrays can be tailored to achieve this level of total monocytes capture in a chip having four separate capture compartments with the footprint of that shown in FIG. 11A.

The efficacy of monocyte capture will be characterized by measuring the composition (% purity) of CD14+ cells captured within the microchannels and the capture efficiency (number of CD14+ cells recovered following purification divided by number of CD14+ cells in whole blood injected into the device) via flow cytometry. A range of flow rates between 5-15 µL/min will be examined using the custom-designed integrated pump to maximize both purity and efficiency, with greater emphasis on the former. A minimum purity level of 95% is identified as a milestone for characterization.

The monocytes adhered within the culture chips are perfused with culture medium containing no cytokines over a period of 6-8 days to verify the ability of the chip to maintain cells in a viable state. All coating materials and device components are sterilized by autoclaving. For culture medium (RPMI 1640) perfusion, flow rates in the range of 5-15 µL/min are tested with the objective of determining if any cell detachment occurs at the higher flow rate range. The cells captured within the microchannel will deposit extracellular matrix proteins and become strongly adhered 12-24 hours after capture and that viability are retained for the full 6-8 day period to be examined. A milestone of <10% cell loss via detachment and viability on chip at 100% represents successful monocyte adherence.

Automation and flow control capability will be designed at the level of an individual chip of the size shown in FIG. 11A. A key strength of this chip design is the highly compact size of the pump. In contrast to the comparatively large system shown in FIGS. 14A-14E, automation at the single chip level will be enabled by the use of small components that can be assembled on a compact breadboard. Such small-scale automation is highly desirable in an application such as monocyte-to-DC conversion because this will allow individual chips to be matched with individual patients and for any given number of patients only that number of chips, and no more, will need to be used, thereby ensuring efficient operation. In addition, such automation also allows for efficient space utilization within incubators.

Example 9. Comparison of DCs Generated Conventionally Vs the Inventive System

Figure 15:
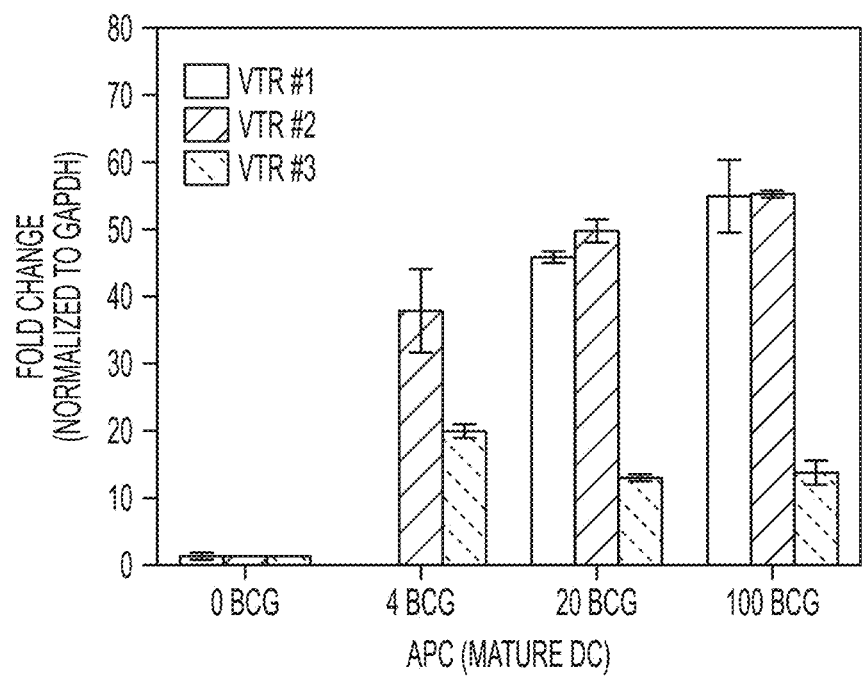
FIG. 15 shows BCG-induced increases in IL2 mRNA at the 24 hour time point measured via RT-PCR following stimulation of memory CD4+ T cells with BCG-infected DCs (20:1 ratio) from three PPD+ individuals.

FIGS. 16A-D show the result of an experiment where memory CD4+ T cells were purified from three PPD+ individuals with Miltenyi negative selection immunomagnetic purification kits resulting in >97% pure memory CD4+ T cells. These cells were stimulated with autologous DCs generated using the conventional culture method (20:1 ratio in culture of T cells to DCs) that were uninfected or infected with a BCG MOI of 4, 20, or 100. Total RNA was harvested at 24, 48, and 72 hours. qRT-PCR for IL2 mRNA was performed to determine what conditions provide the best ability to see BCG-induced changes. FIG. 15 represents a relatively simple way to compare DCs generated conventionally vs the microDEN system.

An experiment was also performed microarray experiments to study the molecular transcriptomes of memory CD4+ T cells induced by oral (PO) and intradermal (ID) BCG in a NIAID VTEU-sponsored trial DMID-01-351. The preliminary data (generated with microarrays experiments with 4 PO and 7 ID BCG recipients) indicate that unique CD4+ T cell molecular signatures are induced by PO vs ID BCG. Illumina Bead Arrays were used for these experiments. Direct ex vivo and BCG re-stimulated transcriptomes pre-vaccination (day 0), at the peak of T cell activation (day 7) and at a later memory/effector time point (day 56). GenePattern Analysis was used to compare pre- and post-vaccination transcriptomes directly ex vivo and after BCG in vitro re-stimulation. FIG. 16A shows heat maps for the top most altered genes directly ex vivo comparing pre-vaccination and day 7 post-vaccination (peak of T cell activation) responses, for PO and ID BCG groups separately. BCG vaccination reproducibly altered expression patterns similarly across individuals within each group. The Venn diagram comparing the unique gene lists identified on day 7 post-vaccination (FIG. 16B), demonstrates that PO and ID BCG induced distinct activation patterns. FIG. 16C shows heat maps for the top most altered genes after BCG restimulation comparing pre-vaccination and day 56 post-vaccination (memory/effector responses), for PO and ID BCG groups separately. The Venn diagram comparing the unique gene lists identified on day 56 post-vaccination (FIG. 16D) demonstrates that PO and ID BCG induced distinct memory patterns. Preliminary GSEA analysis indicated that a set of asthma-associated genes were enriched in PO BCG recipients at both day 7 and 56. These results demonstrate the ability to perform genome-wide expression studies, and to analyze the differential gene profiles induced. Platforms for genome-wide transcriptional analysis have been rapidly improving. The newer RNAseq technology has recently become the new state-of-the art tool for analyzing transcriptomes because of the great reduction in both variation from experiment-to-experiment and false positive responses.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

While the present invention has been described in conjunction with certain preferred embodiments, one of ordinary skill, after reading the foregoing specification, will be able to effect various changes, substitutions of equivalents, and other alterations to the compositions and methods set forth herein.

What is claimed is:

1. A system for producing an immunotherapeutic product, the system comprising:
   a first module configured for processing cellular material associated with a disease of a patient, the first module comprising a fluid inlet port and a separate fluid outlet port;
   a second module configured for generating immune cells, the second module comprising a cell culture chamber, a fluid inlet port, and a separate fluid outlet port disposed on opposite sides of the cell culture chamber, the separate fluid outlet port positioned at a height above the fluid inlet port, wherein the cell culture chamber comprises a monocyte-binding substrate, and wherein the fluid inlet port and the separate fluid outlet port are fluidically coupled to the cell culture chamber and configured to provide flow of a liquid culture medium across the monocyte-binding substrate from the fluid inlet port to the separate fluid outlet port that minimizes mechanical detachment of cells from the monocyte-binding substrate; and
   a third module separately coupled to and in fluidic communication with each of the first and second modules, the third module comprising a first inlet port for fluidic communication with the first module and a separate second inlet port for fluidic communication with the second module such that the third module separately receives a flow of processed cellular material from the first module and separately receives a flow of immune cells from the second module, wherein the third module is configured to co-culture the processed cellular material and the immune cells to produce an immunotherapeutic product.

2. The system of claim 1, wherein the monocyte-binding substrate forms a bottom of the cell culture chamber and comprises a flat surface.

3. The system of claim 1, wherein the monocyte-binding substrate is suitable for binding and differentiating monocytes.

4. The system of claim 1, wherein the fluid inlet port and separate fluid outlet port of the second module are disposed at opposite ends of the cell culture chamber.

5. The system of claim 1, wherein the monocyte-binding substrate comprises a polymer surface that binds monocytes but not other differentiated blood-derived cells.

6. The system of claim 1, further comprising a fourth module comprising an inlet fluidically coupled to an outlet of the third module, the fourth module configured to concentrate the immunotherapeutic product.

7. The system of claim 6, wherein the fourth module is configured as a flow-through chamber.

8. The system of claim 7, wherein the fourth module comprises a filter for filtering out material other than the immunotherapeutic product.

9. The system of claim 7, wherein the fourth module comprises a second inlet for the introduction of a wash fluid.

10. The system of claim 1, wherein the third module is further configured to concentrate the immunotherapeutic product.

11. The system of claim 1, wherein the system is a closed system.

12. The system of claim 11, wherein the closed system is operably coupled to one or more control systems configured to automate and effect movement of fluid through the closed system, wherein the closed system comprises one or more tubes connected to one or more of an actuator, a valve, a flow controller, a sensor, and one or more pumps such that the closed system is configured to allow fluid to be removed from an outlet port of the system for testing without introducing new material or contaminants to the system.

13. The system of claim 1, wherein all components of the system are disposable.

14. The system of claim 1, wherein at least a part of the system comprises disposable components, and wherein the disposable components are housed inside of a non-disposable frame.

15. The system of claim 1, wherein the system is configured to be housed within an incubator.

16. The system of claim 1, wherein the second module is configured to receive a patient blood sample.

17. The system of claim 1, wherein the immune cells are one or more of dendritic cells, macrophages, and B-cells.

* * * * *